US009006412B2

(12) United States Patent
Fujii et al.

(10) Patent No.: US 9,006,412 B2
(45) Date of Patent: Apr. 14, 2015

(54) EXPRESSION VECTOR FOR PSEUDONOCARDIA AUTOTROPHICA

(75) Inventors: Yoshikazu Fujii, Chuo-ku (JP); Tadashi Fujii, Chuo-ku (JP); Akira Arisawa, Chuo-ku (JP); Tomohiro Tamura, Sapporo (JP)

(73) Assignees: Microbiopharm Japan Co., Ltd., Tokyo (JP); National Institute of Advanced Industrial Science and Technology, Tokyo (JP)

( * ) Notice: Subject to any disclaimer, the term of this patent is extended or adjusted under 35 U.S.C. 154(b) by 835 days.

(21) Appl. No.: 13/122,675

(22) PCT Filed: Oct. 5, 2009

(86) PCT No.: PCT/JP2009/067324

§ 371 (c)(1), (2), (4) Date: Apr. 5, 2011

(87) PCT Pub. No.: WO2010/041619

PCT Pub. Date: Apr. 15, 2010

(65) Prior Publication Data

US 2011/0262978 A1 Oct. 27, 2011

(30) Foreign Application Priority Data

Oct. 6, 2008 (JP) ................................. 2008-259317

(51) Int. Cl.

*C07H 21/04* (2006.01)
*C12N 15/00* (2006.01)

(Continued)

(52) U.S. Cl.

CPC ............... *C12P 21/02* (2013.01); *C12N 9/0071* (2013.01); *C12N 9/0073* (2013.01); *C12N 15/74* (2013.01);

(Continued)

(58) Field of Classification Search

CPC .............. C12P 21/02; C12P 7/02; C12P 7/62; C12P 17/06; C12N 9/0071; C12N 9/0073; C12N 15/74; C12Y 114/13013

See application file for complete search history.

(56) References Cited

U.S. PATENT DOCUMENTS 4,346,227 A 8/1982 Terahara et al.
4,410,629 A 10/1983 Terahara et al.

(Continued)

FOREIGN PATENT DOCUMENTS

JP 61-13699 B2 4/1986
JP 62-54476 B2 11/1987

(Continued)

OTHER PUBLICATIONS

Fujii, Yoshikazu, et al., "Isolation of an Enzyme That Activates Vitamin D3: Towards High Efficiency Production of Active Vitamin D3Vitamin-D3", Kagaku to Seibutsu, Aug. 1, 2008, pp. 525-526, vol. 46, No. 8.—English Translation.*

(Continued)

*Primary Examiner* — Reza Ghafoorian
(74) *Attorney, Agent, or Firm* — Sughrue Mion, PLLC

(57) ABSTRACT

An expression vector capable of expressing a foreign gene in *Pseudonocardia autotrophica*; a transformant of *Pseudonocardia autotrophica* produced by using the expression vector; a method for producing a protein by using the transformant; a method for producing an active form of vitamin D3 from vitamin D3, which comprises highly expressing a gene encoding an enzyme involved in the synthesis of the active form of vitamin D3 in a transformant by using the expression vector or the transformant; a method for producing 25-hydroxyvitamin D2 from vitamin D2; and a method for producing pravastatin from compactin, which comprises highly expressing a compactin hydroxylase gene in a transformant by using the expression vector or the transformant.

14 Claims, 8 Drawing Sheets

(51) Int. Cl.

| | |
|---|---|
| ***C12N 15/64*** | (2006.01) |
| ***C12P 21/06*** | (2006.01) |
| ***C12P 21/02*** | (2006.01) |
| ***C12N 9/02*** | (2006.01) |
| ***C12N 15/74*** | (2006.01) |
| ***C12P 7/02*** | (2006.01) |
| ***C12P 7/62*** | (2006.01) |
| ***C12P 17/06*** | (2006.01) |

(52) U.S. Cl.
CPC ... *C12P 7/02* (2013.01); *C12P 7/62* (2013.01); *C12P 17/06* (2013.01); *C12Y 114/13013* (2013.01)

(56) References Cited

U.S. PATENT DOCUMENTS

| | | | |
|---|---|---|---|
| 4,448,979 | A | 5/1984 | Terahara et al. |
| 5,179,013 | A | 1/1993 | Matsuoka et al. |
| 5,766,940 | A | 6/1998 | Yamamoto |
| 8,148,119 | B2 | 4/2012 | Fujii et al. |

FOREIGN PATENT DOCUMENTS

| | | |
|---|---|---|
| JP | H06-253860 | 9/1994 |
| JP | H09-206077 | 8/1997 |
| JP | 2003-235565 | 8/2003 |
| WO | WO 02/099109 | 12/2002 |
| WO | WO 2007/138894 A1 | 12/2007 |

OTHER PUBLICATIONS

Onaka et al., pTOYAMAcos, pTYM18, and pTYM19, Actinomycete-*Escherichia coli* Integrating Vectors for Heterologous Gene Expression, The Journal of Antibiotics, vol. 56 No. 11, Nov. 2003, pp. 950-956.*

Wilkinson et al., Increasing the Efficiency of Heterologous Promoters in Actinomycetes, J. Mol. Microbiol. Biotechnol. (2002) 4(4): 417-426.*

Dobritsa et al. "Genome Identity of Different Nocardia Autotrophica Isolates from *Alnus* spp. Root Nodules and Rhizosphere", Sixth International Symposium on Actinomycetes Biology, Institute of Biochemistry and Physiology of Microorganisms, USSR Academy of Sciences, Aug. 1985, pp. 735-737.

Fujii et al. "Construction of a Novel Expression Vector in *Pseudonocardia* Autotrophica and its Application to Efficient Biotransformation of Compactin to Pravastatin, a Specific HMG-CoA Reductase Inhibitor", Biochemical and Biophysical Research Communications, vol. 404, No. 1, Jan. 7, 2011, pp. 511-516.

Supplementary European Search Report dated Feb. 27, 2012 issued in corresponding European Patent Application No. 09819153.9.

Thiemer et al. "Cloning and Characterization of a Gene Cluster Involved in Tetrahydrofuran Degradation in *Pseudonocardia* sp. Strain K1", Archives of Microbiology vol. 179, No. 4, Apr. 2003, pp. 266-277.

Dietschy, John M., et al., "Regulation of Cholesterol Metabolism", (Second of Three Parts), Medical Progress, May 21, 1970, pp. 1179-1183, vol. 282, No. 21.

Fujii, Yoshikazu, et al., "Vitamin-$D_3$ o Kasseika suru Koso o Bunri, Kasseigata Vitamin-$D_3$ no Kokoritsu Seisan ni Mukete", Kagaku to Seibutsu, Aug. 1, 2008, pp. 525-526, vol. 46, No. 8.

Kannel, William B., "Serum Cholesterol, Lipoproteins, and the Risk of Coronary Heart Disease", Annals of Internal Medicine, Jan. 1971, pp. 1-12, vol. 74, No. 1.

Muramatsu, Masami, et al., (ed), Bunshi Saibo Seibutsugaku Jiten, Feb. 1, 2002, p. 694, 1st edition, Tokyo Kagaku Dojin.

Takeda, Koji, et al., "Application of Cyclodextrin to Microbial Transformation of Vitamin $D_3$ to 25-Hydroxyvitamin $D_3$ and 1$\alpha$, 25-Dihydroxyvitamin $D_3$", Journal of Fermentation and Bioengineering, 1994, pp. 380-382, vol. 78, No. 5.

International Search Report for International Application No. PCT/JP2009/067324 dated Oct. 27, 2009.

Chen et al., "Screening of Compactin-Resistant Microorganisms Capable of Converting Compactin to Pravastatin", Curr. Microbiol., 2006, 53:108-112.

* cited by examiner

WILD-TYPE STRAIN
ACETONE ADDED pTAOR-TRANSFORMED STRAIN
ACETONE ADDED pTAOR3-vdh-TRANSFORMED STRAIN
NO ACETONE ADDED pTAOR3-vdh-TRANSFORMED STRAIN
ACETONE ADDED

EXPRESSION VECTOR FOR PSEUDONOCARDIA AUTOTROPHICA

CROSS REFERENCE TO RELATED APPLICATIONS

This application is a National Stage of International Application No. PCT/JP2009/067324 filed Oct. 5, 2009, which claims priority from Japanese Patent Application No. 2008-259317 filed Oct. 6, 2008, the contents of all of which are incorporated herein by reference in their entirety.

TECHNICAL FIELD

The present invention relates to: an expression vector capable of expressing a foreign gene in *Pseudonocardia autotrophica*; a transformant of *Pseudonocardia autotrophica* produced by using the expression vector; and a method of producing a recombinant protein by using the transformant.

The present invention also relates to a method of producing an active form of the vitamin D group and pravastatin by using the above-mentioned expression vector and transformant.

BACKGROUND ART

*Pseudonocardia autotrophica* is one of actinomycetes and is known to have an ability to convert the vitamin D group such as vitamin D3 from an inactive form to an active form (K. Takeda, J. Ferment. Bioeng., 78(5), 380-382 (1994); Non Patent Document 1).

Vitamin D3 synthesized in biological synthesis systems is usually in an inactive form and shows little physiological activities without further treatments. The inactive form of vitamin D3 is hydroxylated at positions 25 and 1α in the liver and kidney, respectively, and is converted into the active form of vitamin D3 (1α,25-dihydroxyvitamin D3) which shows various physiological activities. Therefore, the hydroxylation reaction from the inactive form to the active form is a particularly important step in expression of a function of vitamin D3.

The active form of vitamin D3 is known to promote absorption of calcium into the body and deposition of calcium to bone tissues, and deficiency of vitamin D3 causes a variety of diseases due to an abnormality of calcium metabolism, such as osteoporosis. Further, in recent years, involvement of the active form of vitamin D3 in cellular differentiation induction and immune regulation has attracted attention. Therefore, the active form of vitamin D3 can be used as a drug for improving or treating a disease caused by the abnormality of calcium metabolism, cellular differentiation, immune regulation, or the like.

As mentioned above, the active form of vitamin D3 can be used as a drug for treating a variety of diseases, but in the case where the active form of vitamin D3 is industrially produced, there are problems such as complex production steps and low yield in chemical synthesis. Therefore, establishment of a more efficient method of producing the active form of vitamin D3 has been desired.

In recent years, an ischemic heart disease caused by coronary arteriosclerosis is increasing in accordance with aging of population and westernization of diets. The incidence rate of the ischemic heart disease is known to increase in the case where a serum cholesterol value exceeds a certain level (W. B. Kannel, Ann. Inntern. Med., 74, 1 (1971); Non Patent Document 2). Cholesterol present in the body includes cholesterol absorbed from a diet and cholesterol biosynthesized in a living body. In the case of humans, it is reported that the amount of cholesterol biosynthesized is 3 to 4 times larger than that of cholesterol absorbed from a diet (J. M. Dietschy, N. Engl. J. Med., 282, 1179 (1970); Non Patent Document 3). Therefore, it is expected that suppression of biosynthesis of cholesterol lowers serum cholesterol value to thereby obtain preventing and treating effects on ischemic heart diseases.

As inhibitors of 3-hydroxy-3-methylglutaryl-coenzyme A (HMG-CoA) reductase, which is a key enzyme of cholesterol biosynthesis, compactin and pravastatin obtained by hydroxylation of compactin at position 6β have been discovered (JP 61-13699 B (U.S. Pat. No. 4,346,227, etc.) (Patent Document 1), U.S. Pat. No. 4,346,227 (Patent Document 2), U.S. Pat. No. 4,410,629 (Patent Document 3), and U.S. Pat. No. 4,448,979 (Patent Document 4)). Pravastatin exhibits an excellent cholesterol biosynthesis inhibitory activity and organ-selective inhibitory activity and hence is used as an anti-hyperlipidemia agent for treating or preventing the ischemic heart disease such as arteriosclerosis.

As methods of synthesizing pravastatin, microbiological methods each including converting compactin used as a raw material into pravastatin by hydroxylation of compactin at position 6β are known (JP 62-54476 B (U.S. Pat. No. 4,346,227, etc.) (Patent Document 5), U.S. Pat. No. 4,346,227 (Patent Document 2), U.S. Pat. No. 4,410,629 (Patent Document 3), U.S. Pat. No. 4,448,979 (Patent Document 4), and U.S. Pat. No. 5,179,013 (Patent Document 6)). However, the microbiological methods are insufficient in terms of pravastatin production ability and production efficiency, and hence establishment of a more efficient method of producing pravastatin has been desired.

The reaction from compactin into pravastatin is hydroxylation as in the case of the reaction from vitamin D3 into the active form of vitamin D3, and the use of *Pseudonocardia autotrophica* to be used in industrial production of the active form of vitamin D3 (K. Takeda, J. Ferment. Bioeng., 78(5), 380-382 (1994); Non Patent Document 1) has been expected to provide an efficient pravastatin production system. However, an expression vector for *Pseudonocardia autotrophica* serving as a host has not been reported.

CITATION LIST

Patent Documents

[PATENT DOCUMENT 1] JP 61-13699 B
[PATENT DOCUMENT 2] U.S. Pat. No. 4,346,227
[PATENT DOCUMENT 3] U.S. Pat. No. 4,410,629
[PATENT DOCUMENT 4] U.S. Pat. No. 4,448,979
[PATENT DOCUMENT 5] JP 62-54476 B
[PATENT DOCUMENT 6] U.S. Pat. No. 5,179,013

Non Patent Documents

[NON PATENT DOCUMENT 1] K. Takeda, J. Ferment. Bioeng., 78(5), 380-382 (1994)
[NON PATENT DOCUMENT 2] W. B. Kannel, Ann. Inntern, Med., 74, 1 (1971)
[NON PATENT DOCUMENT 3] J. M. Dietschy, N. Engl. J. Med., 282, 1179 (1970)

DISCLOSURE OF INVENTION

Problem to be Solved by the Invention

An object of the present invention is to provide: an expression vector capable of expressing a foreign gene in *Pseudonocardia autotrophica*; a transformant of *Pseudonocardia*

*autotrophica* produced by using the expression vector; and a method of producing a protein by using the transformant.

The present invention also relates to a method of producing an active form of vitamin D3 from vitamin D3 by highly expressing a gene encoding an enzyme involved in synthesis of the active form of vitamin D3 in a transformant by using the above-mentioned expression vector and transformant. The converting enzyme also has an activity to hydroxylate vitamin D2 at position 25, and hence the present invention also relates to a method of producing 25-hydroxyvitamin D2 from vitamin D2.

The present invention also relates to a method of producing pravastatin from compactin by highly expressing a compactin hydroxylase gene in a transformant by using the above-mentioned expression vector and transformant.

Means to Solve the Problem

Recently, production of the active form of vitamin D3 using a microorganism has attracted attention instead of production of the active form of vitamin D3 by chemical synthesis. The method includes: giving an inactive form of vitamin D3 to a microorganism capable of converting vitamin D3 from an inactive from to an active form to produce the active form of vitamin D3 in the cells; and separating and purifying the resultant product. One of the microorganisms to be used is *Pseudonocardia autotrophica.*

An enzyme of cytochrome P450 group is known as an enzyme which catalyzes a hydroxylation reaction, and enzymes belonging to cytochrome P450 family have been discovered in a variety of bacteria.

The inventors of the present invention have made intensive studies to perform production of an active form of the vitamin D group using *Pseudonocardia autotrophica* more efficiently, and as a result, the inventors have found out that the active form of the vitamin D group can be produced more efficiently by: introducing a gene of an enzyme involved in synthesis of the active form of the vitamin D group into cells of *Pseudonocardia autotrophica* to be transformed; and expressing the enzyme protein in the transformant.

Further, the inventors of the present invention have made intensive studies to establish a method of producing pravastatin using *Pseudonocardia autotrophica* as a host, and as a result, the inventors have established a method of highly efficiently producing pravastatin by: introducing a gene of an enzyme involved in synthesis of pravastatin into cells of *Pseudonocardia autotrophica*; and expressing the enzyme protein in the transformant.

An expression vector for *Pseudonocardia autotrophica* serving as a host has not been known, and hence the inventors of the present invention has constructed a novel expression vector capable of introducing and expressing the target gene in *Pseudonocardia autotrophica*. Moreover, in order to efficiently produce the target protein in the transformant, the inventors has constructed a novel promoter capable of inducing expression of the target gene by an easy method, and thus completed the present invention.

That is, the present invention relates to the following items [1] to [12].

[1] An expression vector, including a replication initiation region derived from *Pseudonocardia autotrophica*, a multicloning site for introducing an exogenous gene, an exogenous gene introduced into the multicloning site, a promoter, a terminator, and a selection marker, which autonomously replicates in cells of *Pseudonocardia autotrophica* to enable expression of the exogenous gene introduced.

[2] The expression vector according to [1] above, in which the replication initiation region comprises a base sequence represented by SEQ ID NO: 49 or a complementary sequence thereof, or a base sequence having 80% or more homology to the above base sequence or a complementary sequence thereof.

[3] The expression vector according to [1] or [2] above, in which the promoter is induced by acetone to express the exogenous gene.

[4] The expression vector according to [3] above, in which the promoter region comprises a base sequence represented by SEQ ID NO: 26 or a complementary sequence thereof, or a base sequence having 80% or more homology to the above base sequence or a complementary sequence thereof.

[5] The expression vector according to any one of [1] to [4] above, further including a replication initiation region derived from *Escherichia coli*, and being autonomously replicable in both *Pseudonocardia autotrophica* and *Escherichia coli*, and can be used as a shuttle vector.

[6] The expression vector according to [5] above, having an oriT region and can perform transformation by conjugation of *Escherichia coli* S17-1 and *Pseudonocardia autotrophica.*

[7] The expression vector according to any one of [1] to [6] above, in which the exogenous gene is a gene encoding vitamin D hydroxylase or a gene encoding compactin hydroxylase.

[8] A transformant of *Pseudonocardia autotrophica* having introduced thereinto the expression vector according to any one of [1] to [7] above.

[9] A method of producing a protein comprising: introducing the expression vector according to any one of [1] to [7] above into *Pseudonocardia autotrophica* to be transformed; and expressing the exogenous gene in the resultant transformant to produce a protein.

[10] A method of producing an active form of vitamin D including: transforming *Pseudonocardia autotrophica* with the expression vector according to any one of [1] to [7] above, having introduced thereinto a vitamin D hydroxylase gene as an exogenous gene; and using the resultant transformant.

[11] The method of producing an active form of vitamin D according to [10] above, in which the active form of vitamin D is 25-hydroxyvitamin D2, 25-hydroxyvitamin D3, or $1\alpha$,25-dihydroxyvitamin D3.

[12] A method of producing pravastatin including: transforming *Pseudonocardia autotrophica* with the expression vector according to any one of [1] to [7] above, having introduced thereinto a compactin hydroxylase gene as an exogenous gene; and using the resultant transformant to produce pravastatin from compactin.

Advantageous Effects of Invention

The expression vector of the present invention has a replication initiation region which enables autonomous replication in *Pseudonocardia autotrophica*, and hence can introduce and express the target gene into *Pseudonocardia autotrophica.*

Moreover, when a transformant of *Pseudonocardia autotrophica* having introduced thereinto the expression vector of the present invention is used, an enzyme gene involved in synthesis of an active form of vitamin D3 in the transformant can be highly expressed. Therefore, it is possible to produce the active form of vitamin D3 from vitamin D3 more efficiently and at a higher yield compared with a conventional system for producing the active form of vitamin D3 using *Pseudonocardia autotrophica.*

In addition, when the transformant of *Pseudonocardia autotrophica* having introduced thereinto the expression vector of the present invention is used, an enzyme gene involved in synthesis of pravastatin in the transformant can be highly expressed. Therefore, it is possible to produce pravastatin from compactin highly efficiently at a high yield using *Pseudonocardia autotrophica.*

BRIEF DESCRIPTION OF DRAWINGS

FIG. 5A continues to FIG. 5B.

FIG. 5B is a diagram illustrating the construction of the VDH expression vectors.

DESCRIPTION OF EMBODIMENTS

Figure 1:
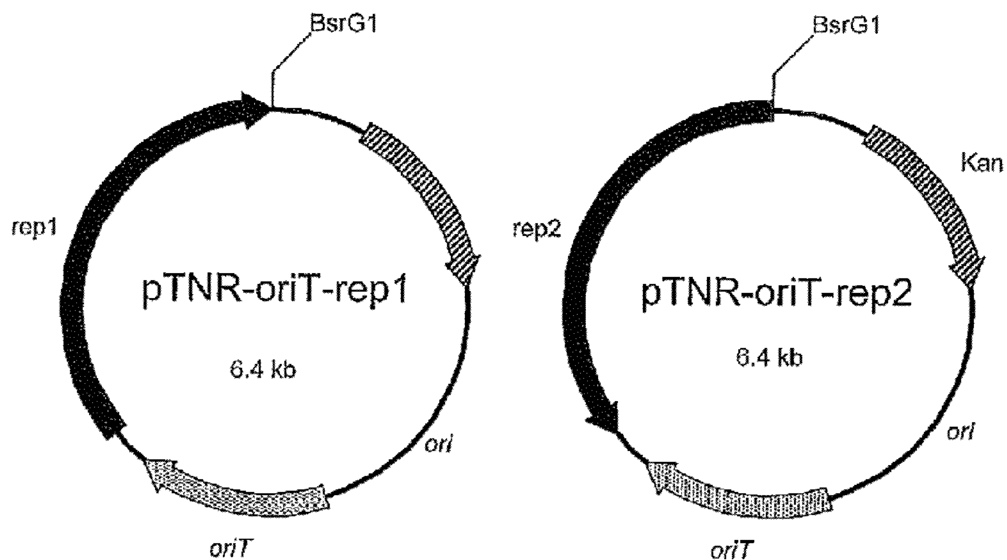
FIG. 1 is a schematic view illustrating vectors of a plasmid pTNR-oriT-rep1 and a plasmid pTNR-oriT-rep2.

Hereinafter, the expression vector, transformant, and method of producing a protein of the present invention are described in more detail.

1. Expression Vector

The expression vector of the present invention is an expression vector, including a replication initiation region derived from *Pseudonocardia autotrophica*, a multicloning site for introducing an exogenous gene, an exogenous gene introduced into the multicloning site, a promoter, a terminator, and a defective selection marker, and autonomously replicates in cells of *Pseudonocardia autotrophica* to enable expression of the exogenous gene introduced.

(1) Identification of Replication Initiation Region

First, the replication initiation region of *Pseudonocardia autotrophica* in the expression vector of the present invention is described.

The term "replication initiation region" as used herein refers to a region essential for replication of a plasmid in cells of *Pseudonocardia autotrophica* (hereinafter, in this description, also referred to as "essential region for replication"). That is, a plasmid including the "replication initiation region" replicates in the cells of *Pseudonocardia autotrophica*, and the plasmid is distributed to daughter cells in cell division and replicates in the cells.

The replication initiation region can be identified by isolating a plasmid carried by a bacterium belonging to the genus *Pseudonocardia*, and identifying the replication initiation region in the plasmid. Bacteria belonging to the genus *Pseudonocardia*, which have been isolated and retained hitherto, are collected from the culture collection or the like and cultured to extract plasmids, and a bacterial strain carrying the plasmid is identified. The DNA sequence of the plasmid extracted is determined, and homology search is performed to predict a replication initiation region. The replication initiation region is identified by transforming *Pseudonocardia autotrophica* with the plasmid having introduced thereinto the region, and confirming that *Pseudonocardia autotrophica* carries the plasmid.

According to the above-mentioned method, the base sequence of a replication initiation region, which is derived from *Pseudonocardia autotrophica* and is represented by SEQ ID NO: 49, can be obtained.

The replication initiation region derived from *Pseudonocardia autotrophica* in the expression vector of the present invention preferably includes a base sequence represented by SEQ ID NO: 49 or a complementary sequence thereof, or a base sequence having 80% or more, more preferably 90% or more homology to the base sequence or a complementary sequence thereof.

(2) Construction of Expression Vector

The expression vector of the present invention is constructed so as to include the replication initiation region derived from *Pseudonocardia autotrophica*, a multicloning site for introducing an exogenous gene, an exogenous gene introduced into the multicloning site, a promoter, a terminator, and a defective selection marker.

The multicloning site and terminator to be used in the expression vector of the present invention are not particularly limited, and the promoter may be an acetone-inducible promoter, a thiostrepton-inducible promoter (N. Nakashima, Appl. Environ. Microbiol., 5557-5568 (2004)), an ermE promoter (T. Schmitt-John, Appl. Microbiol. Biotechnol., 36, 493-498 (1992)), or the like. In addition, the defective selection marker may be a gene which is used for a general plasmid, the host of which is a microorganism, such as an ampicillin-resistant gene, a kanamycin-resistant gene, a chloramphenicol-resistant gene, or an apramycin-resistant gene.

When the expression vector of the present invention is used, an exogenous target gene can be introduced into *Pseudonocardia autotrophica* to be transformed. Further, when the expression vector of the present invention is used, the exogenous gene can be expressed in the transformant of *Pseudonocardia autotrophica* to produce a gene product such as a protein of interest.

2. Promoter

The promoter in the expression vector of the present invention is not particularly limited, but preferably has the sequence of a promoter which is induced by acetone and is derived from *Pseudonocardia autotrophica.*

When the expression vector of the present invention has the above-mentioned acetone-inducible promoter, it is possible to induce expression of the target gene by addition of acetone and to produce a protein of interest by a low-cost and easy method at a high yield.

(1) Identification of Acetone-Inducible Promoter

First, a promoter induced by acetone is identified as a promoter which is derived from *Pseudonocardia autotrophica* and can induce the target gene easily and at a low cost.

Acetone is added to a culture medium of *Pseudonocardia autotrophica* at a concentration of 1% (v/v), and *Pseudonocardia autotrophica* is further cultured. Then, a protein highly induced, compared with a case where acetone is not added, is identified as a band of two-dimensional electrophoresis. An acetone-inducible promoter can be identified by analyzing the amino acid sequence of the band to perform an analysis of a gene encoding the protein and identifying a promoter sequence present in the upstream of the gene encoding the protein.

The acetone-inducible promoter sequence which was represented by SEQ ID NO: 26 and was derived from *Pseudonocardia autotrophica* was obtained by the above-mentioned method.

The promoter sequence in the expression vector of the present invention is preferably a base sequence represented by SEQ ID NO: 26 or a complementary sequence thereof, or a base sequence having 80% or more, more preferably 90% or more homology to the above base sequence or a complementary sequence thereof.

(2) Construction of Acetone-Inducible Expression Vector

An acetone-inducible vector is constructed by inserting the acetone-inducible promoter into the upstream of a multicloning site in a plasmid. A strain transformed with the acetone-inducible vector constructed is cultured for about 2 days, and 0.5% or 1% acetone is added to the culture medium, to thereby highly express the gene inserted into the multicloning site.

The acetone-inducible expression vector of the present invention has the above-mentioned acetone-inducible promoter sequence. Therefore, when acetone is added to the expression system, it is possible to express the exogenous gene inserted into the downstream of the promoter region in *Pseudonocardia autotrophica* inductively at high efficiency.

3. Construction of Shuttle Vector

The expression vector of the present invention may be a complex vector (shuttle vector) to adapt the vector to a plurality of host cells.

Examples of the shuttle vector to be used in the present invention include a vector which can be introduced into both *Escherichia coli* and *Pseudonocardia autotrophica* and can express a foreign gene in cells of the hosts.

In the case of using the expression vector of the present invention as the shuttle vector, the shuttle vector is preferably an expression vector which includes not only the above-mentioned replication initiation region derived from *Pseudonocardia autotrophica* but also a replication initiation region derived from *Escherichia coli*, and can autonomously replicate in both *Pseudonocardia autotrophica* and *Escherichia coli*. The replication initiation region derived from *Escherichia coli* is preferably the on for *E. coli* (the base sequence at positions 2,372 to 3,487 in SEQ ID NO: 46) illustrated in FIG. 6.

Figure 6:
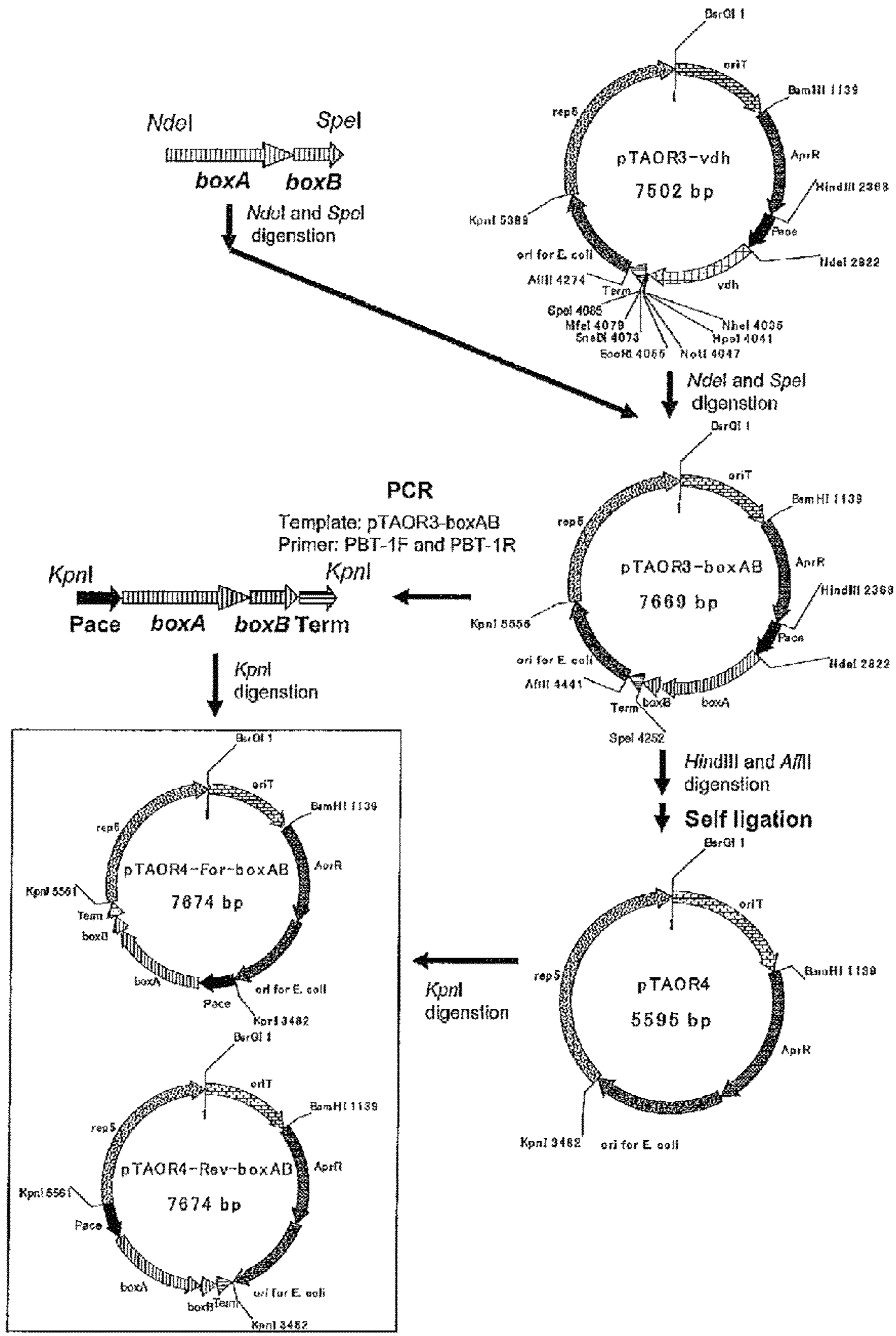
FIG. 6 is a diagram illustrating construction of BoxAB expression vectors.

The shuttle vector can be prepared by constructing a plasmid including a replication initiation region derived from *Escherichia coli* and a replication initiation region derived from *Pseudonocardia autotrophica*. In FIG. 6, the on for *E. coli* and rep5 are the regions.

In order to conjugate *Escherichia coli* and *Pseudonocardia autotrophica*, the vector preferably includes a conjugation region. For example, in the case of *Escherichia coli* S17-1 and *Pseudonocardia autotrophica*, a shuttle vector having an oriT region can conjugate and transform the bacteria.

4. Exogenous Gene

The expression vector of the present invention includes an exogenous gene. The exogenous gene which can be used in the present invention is not particularly limited, and examples thereof include a cytochrome P450 gene typified by a gene encoding vitamin D hydroxylase and a gene encoding compactin hydroxylase, and a hydrolase and dehydrogenase to be used for conversion of another compound. Of those, the cytochrome P450 gene such as the gene encoding vitamin D hydroxylase or the gene encoding compactin hydroxylase is preferred.

5. Construction of Transformant

Next, construction of a transformant of *Pseudonocardia autotrophica* using the expression vector of the present invention is described.

The transformant of the present invention is obtained by introducing the above-mentioned expression vector of the present invention into *Pseudonocardia autotrophica*.

In the present invention, a method of introducing the vector is not particularly limited, but may be a known genetic engineering technique, and conjugation, a protoplast method, a competent cell, an electroporation method, and the like are preferably used. Of those, the conjugation and protoplast method are more preferred. For example, in the case where the expression vector of the present invention is the above-mentioned shuttle vector, a transformant of *Pseudonocardia autotrophica* can be obtained by introducing the expression vector into *Escherichia coli* S17-1 to transform the bacterium and performing conjugation using the resultant transformant of *Escherichia coli* S17-1 and *Pseudonocardia autotrophica*.

First, *Escherichia coli* strain S17-1 transformed with the expression vector of the present invention and *Pseudonocardia autotrophica* are separately cultured until the respective logarithmic growth phases, and the culture media are mixed. The bacterial cells are precipitated by slow centrifugation and cultured in an LB plate medium containing no antibiotics for 1 day to perform conjugation. The bacterial cells are scraped off and cultured in an LB plate medium containing an antibiotic to select a transformant. In this case, in order to grow only *Pseudonocardia autotrophica* transformed, nalidixic acid which inhibits growth of *Escherichia coli* is added in advance to the LB plate medium.

6. Method of Producing Protein Using Transformant

A protein of interest can be produced by introducing an exogenous gene into *Pseudonocardia autotrophica* using the expression vector of the present invention and expressing the exogenous gene in the resultant transformant of *Pseudonocardia autotrophica*.

As a technique for expressing the target gene in a transformant to produce a protein, a known technique may be appropriately selected and used depending on properties of the promoter or the like in the expression vector.

(1) Method of Producing Active Form of the Vitamin D Group Using Transformant

Next, a method of producing an active form of the vitamin D group using the expression vector and transformant of the present invention is described.

The term "the vitamin D group" as used herein refers to vitamin D3, vitamin D2, and the like.

The method of producing the active form of the vitamin D group of the present invention includes: inserting a vitamin D hydroxylase gene into the above-mentioned expression vector to transform *Pseudonocardia autotrophica* with the vector; and inductively expressing the vitamin D hydroxylase gene in the resultant transformant to convert the vitamin D group into the active form of the vitamin D group.

Compared with the vitamin D group, the active form of the vitamin D group has a structure hydroxylated at positions 25 and 1α. Specifically, the active form of vitamin D3 is 25-hydroxyvitamin D3 or 1α,25-dihydroxyvitamin D3, and the active form of vitamin D2 is 25-hydroxyvitamin D2.

In this case, the vitamin D hydroxylase which may be used in the method includes VDH derived from *Pseudonocardia autotrophica*, P450SU-1 derived from *Streptomyces griseolus*, and CYP2R1, CYP27A1, and CYP27B1 derived from mammals, all of which have been reported to catalyze hydroxylation of vitamin D3 (N. Sawada, Biochem. Biophys. Res. Commun., 320, 156-164 (2004), E. Uchida, Biochem. Biophys. Res. Commun., 320, 156-164 (2004), N. Strushkevich, J. Mol. Biol., 380, 95-106 (2008)). Of those, VDH which is a causative enzyme of production of the active form of vitamin D3 using *Pseudonocardia autotrophica* is preferably used.

The method of producing the active form of the vitamin D group using a transformant of *Pseudonocardia autotrophica* has been established by adding a step of induction by acetone to a method of producing the active form of the vitamin D group using a wild-type *Pseudonocardia autotrophica*. *Pseudonocardia autotrophica* transformed with the expression vector obtained by inserting vitamin D hydroxylase into the multicloning site is cultured for 2 days, and 1% acetone is added to inductively express the vitamin D hydroxylase, followed by culture for 1 day. The vitamin D group preliminarily mixed with cyclodextrin is added to the culture medium to perform conversion, to thereby produce the active form of the vitamin D group.

According to the method of producing the active form of the vitamin D group of the present invention, it is possible to introduce an exogenous hydroxylase gene into *Pseudonocardia autotrophica* and to highly express the hydroxylase gene in *Pseudonocardia autotrophica* by induction of expression, and hence the active form of the vitamin D group can be produced more efficiently at a high yield compared with a conventional system for producing the active form of the vitamin D group using a microorganism.

(2) Method of Producing Pravastatin Using Transformant

Next, a method of producing pravastatin using the expression vector and transformant of the present invention is described.

The method of producing pravastatin of the present invention includes: inserting a compactin hydroxylase gene into the above-mentioned expression vector to transform *Pseudonocardia autotrophica* with the vector; and inductively expressing the compactin hydroxylase gene in the resultant transformant to convert compactin into pravastatin.

Figure 9:
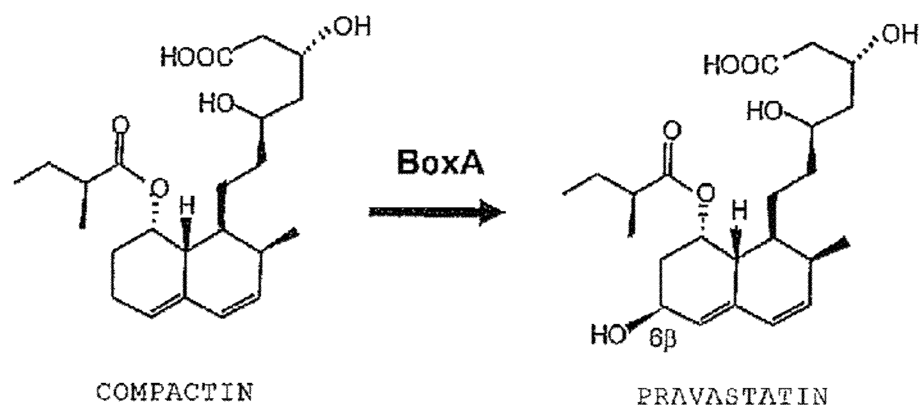
FIG. 9 is a diagram illustrating conversion from compactin to pravastatin.

Compactin and pravastatin are cholesterol biosynthesis inhibitors. As shown in FIG. 9, pravastatin can be obtained by introducing a hydroxy group into compactin.

Pravastatin is preferably produced by converting compactin by adding compactin to a culture medium of *Pseudonocardia autotrophica* transformed with the expression vector obtained by inserting a compactin hydroxylase gene into a multicloning site.

As the compactin hydroxylase gene, boxA derived from *Streptomyces* sp. TM-7, P450sca-2 gene derived from *Streptomyces carbophilus* SANK strain 62585 (JP 06-70780 A), or the like may be used.

The method of producing pravastatin using a transformant of *Pseudonocardia autotrophica* has been established according to the method of producing the active form of vitamin D using a transformed strain of *Pseudonocardia autotrophica*. *Pseudonocardia autotrophica* transformed with an expression vector obtained by inserting boxAB genes encoding compactin hydroxylase and ferredoxin which is an electron transport system protein of P450 present in the downstream of the compactin hydroxylase into a multicloning site is cultured for 2 days, and 1% acetone is added to inductively express the compactin hydroxylase, followed by culture for 1 day. Compactin is added to the culture medium at a final concentration of 4,000 mg/L to perform conversion, to thereby produce pravastatin. If the amount of compactin decreases by conversion, compactin is added again to perform conversion, to thereby accumulate 13 g/L of pravastatin.

According to the method of producing pravastatin of the present invention, it is possible to introduce an exogenous hydroxylase gene into *Pseudonocardia autotrophica* and to highly express the hydroxylase gene in *Pseudonocardia autotrophica* by induction of expression, and hence pravastatin can be produced more efficiently at a high yield compared with a conventional system for producing pravastatin using a microorganism.

EXAMPLES

Hereinafter, the present invention is described in more detail by way of specific examples. However, the present invention is not limited to the examples. It should be noted that the percent (%) in the following examples means a percent by weight in the description of media and means a percent by volume in the description of mobile phases for HPLC.

Production Example

Construction of Expression Vector and Transformant (1) Extraction of Plasmid from *Pseudonocardia autotrophica* DSM 43082 Strain 25 strains of *Pseudonocardia autotrophica* (respective strains of DSM535, DSM43082, DSM43083, DSM43084, DSM43085, DSM43086, DSM43087, DSM43088, DSM43090, DSM43091, DSM43094, DSM43095, DSM43096, DSM43097, DSM43098, DSM43099, DSM43100, DSM43102, DSM43103, DSM43104, DSM43105, DSM43106, DSM43107, DSM43129, and DSM43558) obtained from Deutsche Sammlung von Mikroorganismen and Zellkulturen GmbH (DSMZ) were each inoculated in an LB medium (1.0% Bacto Tryptone, 0.5% yeast extract, 1.0% sodium chloride) and subjected to shaking culture in the presence of two glass beads (diameter: 5 mm) at 30° C. After culture, the collected bacterial cells were suspended in P1 buffer (Plasmid Miniprep kit, QIAGEN) containing lysozyme at a final concentration of 1 mg/ml and allowed to react at 37° C. for 30 minutes, and P2 buffer was added to lyse the bacteria, followed by purification of plasmids according to the instructions of the kit. The purified DNAs were subjected to agarose electrophoresis to detect plasmid-like DNA bands from 11 strains (DSM535, DSM43082, DSM43085, DSM43086, DSM43087, DSM43095, DSM43102, DSM43104, DSM43105, DSM43107, and DSM43129). The purified plasmids derived from the strains DSM43082, DSM43085, and DSM43095 selected from the above-mentioned strains were treated with a restriction enzyme, and DNA cleavage types were compared. Then, the DNA plasmid derived from the strain DSM43082 was further analyzed.

It should be noted that *Pseudonocardia autotrophica* strain DSM43082 was obtained from Deutsche Sammlung von Mikroorganismen and Zellkulturen GmbH (DSMZ; Inhoffenstrasse 7 B, 38124 Braunschweig GERMANY) on May 9, 2005 (contract date), but the place of sampling, date of sampling, isolation source, isolator, and date of isolation are unknown.

The plasmid derived from the strain DSM43082 was digested with a restriction enzyme KpnI to prepare DNA fragments, and fragments of about 0.9 kb and about 2.0 kb out of the resultant DNA fragments were separated and purified by an agarose gel and cloned into pBluescript SK(+) (Stratagene Corporation). The purified plasmid was subjected to a sequence reaction using T7 and T3 primers (SEQ ID NOS: 8 and 9) to determine a partial sequence of the cloned DNA fragment. Subsequently, primers were newly designed based on the partial information, and a sequence analysis was performed using the plasmid purified from the strain DSM43082 as a template. The sequencing was performed by a primer walking method, and the analysis was repeated until base sequence analysis initiation points of both the sense and antisense strands were confirmed, that is, until the DNA was confirmed to be a circular DNA. As a result, the resultant plasmid pPA43082 was found to be a circular DNA of 8047 bp (SEQ ID NO: 12).

(2) Identification of Essential Region for Replication in *Pseudonocardia autotrophica* in Sequence of pPA43082

Figure 2:
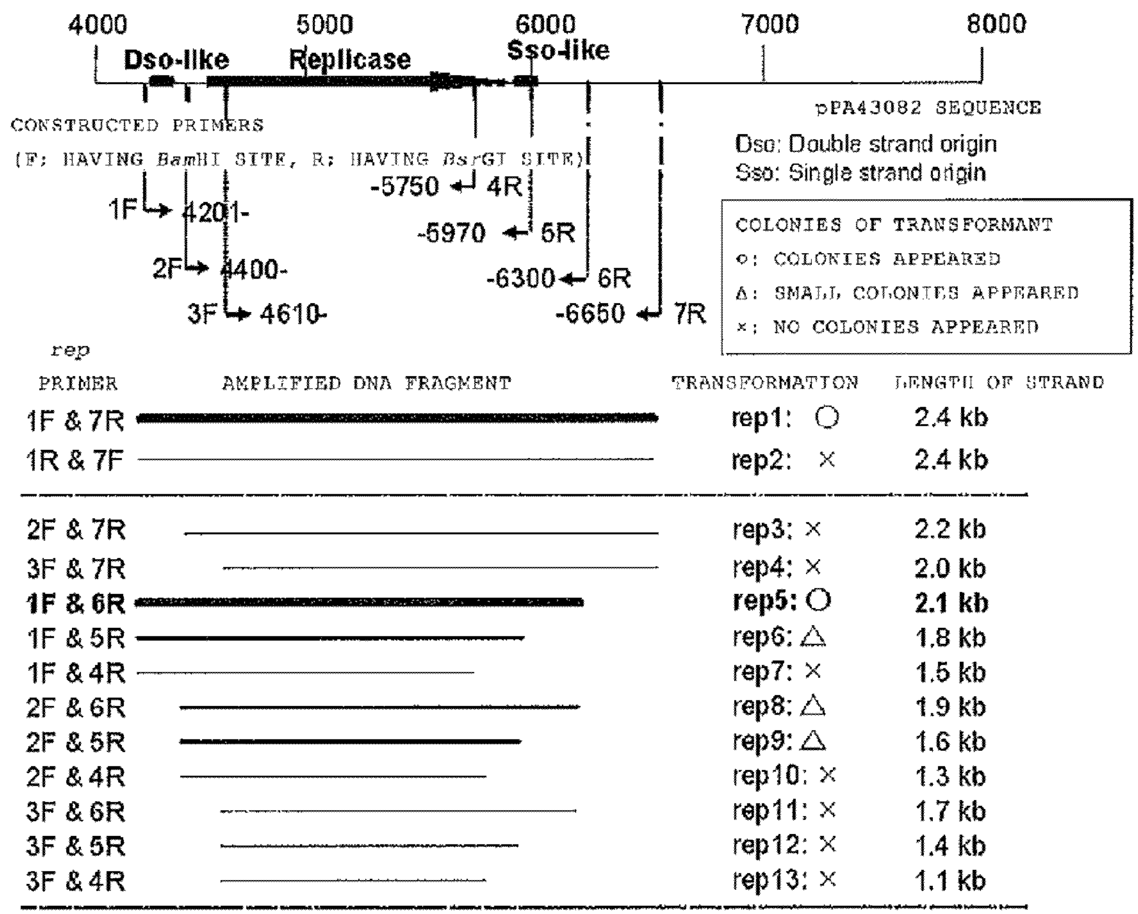
FIG. 2 is a table showing identification of replication initiation regions.

The DNA sequence of the plasmid pPA43082 derived from *Pseudonocardia autotrophica* DSM43082 shown in SEQ ID NO: 12 was suggested to include a Sso (single-strand origin)-like sequence (SEQ ID NO: 52), a Dso (double-strand origin)-like sequence (SEQ ID NO: 51), and a Replicase gene (SEQ ID NO: 50) at about 4 kb to 6 kb region and to have a replication pattern of Rolling circle (S. A. Khan, Microbiol. Mol. Biol. Rev., 442-455 (1997)) (FIG. 2). In order to create an expression vector, it is necessary to include a region essential for replication, and a region at least necessary for replication was identified. That is, a test was performed to examine whether *Pseudonocardia autotrophica* was able to be transformed with a plasmid constructed by: amplifying DNA fragments with different lengths using the pPA43082 as a template by PCR; and replacing the DNA fragments using an istAB gene and BsrGI and BglII sites of pTNR-oriT (K. I. Sallam, Gene, 386, 173-182 (2007)).

First, pTNR-oriT was digested with BsrGI and BglII, and a DNA fragment of about 4.0 kb was cut out by agarose gel electrophoresis and purified by Wizard SV Gel and PCR Clean-Up System (Promega KK.), to thereby obtain DNA fragment-1.

Next, in order to amplify essential regions for replication of pPA43082 by PCR, sets of primers: rep-1F (having BamHI site: SEQ ID NO: 17) and rep-7R (having BsrGI site: SEQ ID NO: 18); and rep-1R (having BsrGI site: SEQ ID NO: 19) and rep-7F (having BamHI site: SEQ ID NO: 20) were created. The two sets of primers were used to perform PCR reactions using pPA43082 as a template. The PCR reactions were performed using KOD plus (TOYOBO CO., LTD.) and a PCR amplification device (Biometra, T Gradient) by repeating a three-step reaction including: denaturation at 98° C. for 20 seconds; annealing at 55° C. for 30 seconds; and elongation at 68° C. for 3 minutes, 25 times. As a result, DNA fragments with lengths of about 2.4 kb were amplified. The fragment amplified from rep-1F and rep-7R was defined as DNA fragment-2, and the fragment amplified from rep-1R and rep-7F was defined as DNA fragment-3. The PCR reaction solutions were subjected to agarose gel electrophoresis, and DNA fragments of about 2.4 kb were cut out and collected by Wizard SV Gel and PCR Clean-Up System (PromegaKK.). The collected DNA fragments were ligated to DNA fragment-1 using DNA Ligation kit ver 2.1 (TAKARA BIO INC.), and *Escherichia coli* strain DH5α (TAKARA BIO INC.) was transformed. After that, LB agar medium (1.5% agar) containing kanamycin (25 μg/ml) was used to select transformed *Escherichia coli*. The thus-separated colonies of the transformed *Escherichia coli* were cultured in LB liquid medium containing kanamycin (25 μg/ml). The plasmid DNA was purified from the proliferated transformed *Escherichia coli* using Wizard Plus SV Minipreps DNA Purification system (Promega KK.), to thereby obtain a plasmid pTNR-oriT-rep1 having inserted thereinto DNA fragment-2, and a plasmid pTNR-oriT-rep2 having inserted thereinto DNA fragment-3 (FIG. 1). *Escherichia coli* S17-1 was transformed with pTNR-oriT-rep1 and pTNR-oriT-rep2, and the transformed strains were cultured in LB medium containing 25 μg/ml kanamycin at 37° C. for 10 hours. 200 μl of the culture medium of the transformed strain of *Escherichia coli* S17-1 were mixed with 500 μl of a culture medium of *Pseudonocardia autotrophica* cultured in LB medium at 30° C. for 80 hours, and the mixture was centrifuged at 7,000 rpm for 30 seconds. 500 μl of the supernatant was discarded, and the precipitates were suspended in the residual supernatant, and the whole was applied to LB agar medium. In order to transform *Pseudonocardia autotrophica* with pTNR-oriT-rep1 and pTNR-oriT-rep2 by conjugation, culture was performed at 30° C. for 24 hours, and the bacterial cells on the agar medium were suspended in 2 ml of LB medium. 200 μl of the suspension was applied to LB agar medium containing 200 μg/ml kanamycin and 50 μg/ml nalidixic acid to select a transformed strain of *Pseudonocardia autotrophica*. The cells were cultured at 30° C. for 10 days, and as a result, a strain of *Pseudonocardia autotrophica* transformed with pTNR-oriT-rep1 was obtained, but a strain of *Pseudonocardia autotrophica* transformed with pTNR-oriT-rep2 was not obtained. The results suggested that the direction of the essential region for replication in pTNR-oriT was important, and it was decided that the following identification of the essential region for replication was performed in the rep1 direction.

In order to identify the essential region for replication, primers rep-2F (SEQ ID NO: 21), rep-3F (SEQ ID NO: 22), rep-4R (SEQ ID NO: 23), rep-5R (SEQ ID NO: 24), and rep-6R (SEQ ID NO: 25) were created. The primers were used as sets shown in FIG. 2 to perform PCR using pPA43082 as a template. PCR reactions were performed using KODplus (TOYOBOCO., LTD.) and the PCR amplification device (Biometra, T Gradient) by repeating a three-step reaction including: denaturation at 98° C. for 20 seconds; annealing at 55° C. for 30 seconds; and elongation at 68° C. for 3 minutes, 25 times. As a result, DNA fragments with lengths shown in FIG. 2 were amplified. DNA fragments amplified in the same way as described above were inserted into the BsrGI site and BglII site of pTNR-oriT to create a plasmid, and *Pseudonocardia autotrophica* was transformed by conjugation. In the range examined, a DNA sequence including rep5 (nucleotides at positions 4,201 to 6,300 of pPA48032; 2.1 kb) was considered to be essential for replication in *Pseudonocardia autotrophica.*

*Pseudonocardia autotrophica* transformed with the plasmid pTNR-oriT-rep5 was cultured in 25 ml of LB medium containing 200 μg/ml kanamycin and 50 μg/ml nalidixic acid at 30° C. for 72 hours. 7 ml of the culture medium were centrifuged, and a plasmid DNA was purified using Wizard Plus SV Minipreps DNA Purification system (Promega KK.), to thereby obtain plasmid-1. The plasmid solution was subjected to agarose gel electrophoresis, and as a result, no band was observed. However, when *Escherichia coli* DH5α (TAKARA BIO INC.) was transformed using the plasmid solution, colonies were obtained on LB agar medium containing 25 μg/ml kanamycin. The colonies were cultured in LB medium containing 25 μg/ml kanamycin, and a plasmid DNA was purified using Wizard Plus SV Minipreps DNA Purification system (Promega KK.), to thereby obtain plasmid-2. When pTNR-oriT-rep5 and the extracted plasmid-2 were digested with BsrGI and BglII respectively, DNA fragments of 5.1 kb and 1.1 kb were obtained from the samples.

The results suggested that the plasmid pTNR-oriT-rep5 did not undergo a structural change in *Pseudonocardia autotrophica* and was conserved.

(3) Identification of Acetone-Inducible Promoter Sequence

Figure 3:
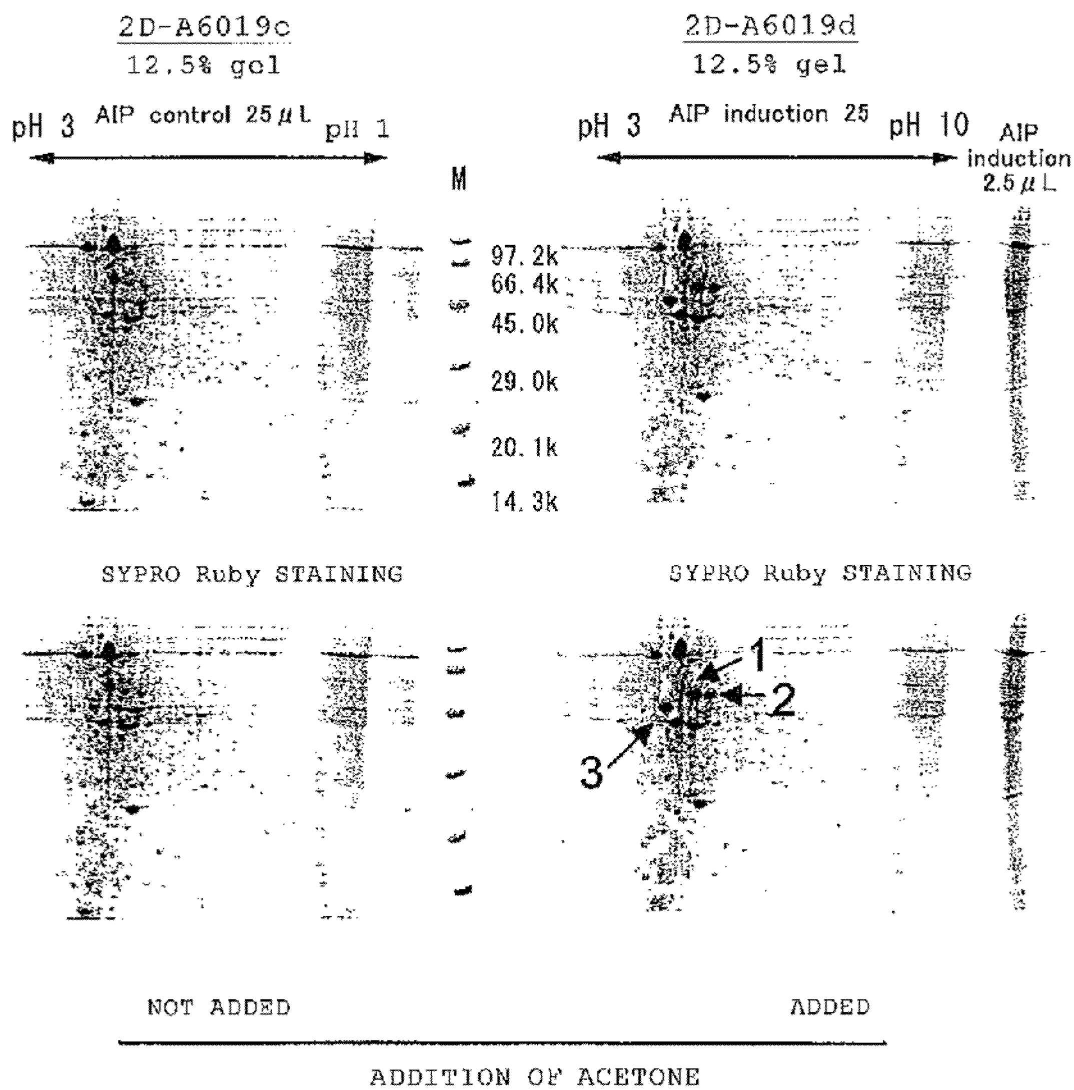
FIG. 3 is two-dimensional electrophoresis images showing identification of acetone-inducible proteins.

*Pseudonocardia autotrophica* strain NBRC12743 was inoculated into 150 ml of LB medium and cultured at 30° C. for 102 hours while shaking at 220 rpm. It should be noted that *Pseudonocardia autotrophica* strain NBRC12743 was obtained from Institute for Fermentation (IFO, now National Institute of Technology and Evaluation (NBRC, Department of Biotechnology, NITE Biological Resource Center; 2-5-8 Kazusakamatari, Kisarazu, Chiba 292-0818, Japan)) before 1987, but the place of sampling, date of sampling, isolation source, isolator, and date of isolation are unknown. 10 ml of the culture medium were inoculated into two flasks each containing 200 ml of LB medium, and the bacterium was cultured at 30° C. for 70 hours while shaking at 220 rpm. 1 ml of acetone was added to one of the two culture media, and the bacterium was further cultured at 30° C. for 24 hours while shaking at 220 rpm. The culture media were centrifuged at 7,000 rpm for 10 minutes to obtain bacterial cells as precipitates. The cells were suspended in 20 ml of CV buffer (50 mM potassium phosphate buffer, pH 7.4, 10% Glycerol) to prepare 10-fold concentrated cell suspensions. A procedure of vigorously shaking 1 ml of the cell suspensions using Fast-PROTEIN BLUE kit (Funakoshi Corporation) by FastPrep FP120 (BIO101, SAVANT) at a speed of 6.0 for 40 seconds was repeated three times, to thereby break the cells. The broken cell suspensions were centrifuged at 13,000 rpm for 10 minutes, to thereby obtain cell-free extracts as supernatants. 25 μl of each sample was mixed with a swelling solution (7 M Urea, 2 M Thiourea, 20 mM Dithiothreitol (DTT), 2 mMTris-(2-cyanoethyl)phosphine, 2% CHAPS, 0.2% (v/v) BioLyte 3-10) containing Bromophenol Blue (BPB) to prepare a sample for two-dimensional electrophoresis. IPG ReadyStrip gel (7 cm, pH3-10NL, BIO-RAD; hereinafter, referred to as IPG gel) was swollen for 12 hours with 125 μl of the sample for two-dimensional electrophoresis. The gel was subjected to electrophoresis (first dimension, isoelectric focusing electrophoresis), and the IPG gel was equilibrated with an equilibration buffer A (50 mM Tris-HCl buffer, pH 8.5, 6 M Urea, 30% Glycerol, 2% SDS, 1% DTT, and 0.005% BPB) for 15 minutes and then with an equilibration buffer B (50 mM Tris buffer, pH 8.5, 6 M Urea, 30% Glycerol, 2% SDS, 4.5% Iodoacetamide, and 0.005% BPB) for 15 minutes. After that, the equilibrated IPG gel was set on 12.5% homogeneous gel (7×6.5 cm), and the second-dimensional electrophoresis was performed (second dimension, SDS polyacrylamide gel electrophoresis). After electrophoresis, the gel was stained with SYPRO Ruby (Invitrogen), and images were captured by Molecular Imager FX (BIO-RAD). After that, spot patterns of the respective samples were compared by visual observation. As a result, three kinds of bands of proteins, the expression each of which increased by addition of acetone, were observed (FIG. 3: Spots 1 to 3). The expression level of Spot 1 estimated to have a molecular weight of about 55 kDa most increased by addition of acetone. Therefore, a part of the gel corresponding to the protein band was cut out, and Tris buffer of pH 8.5 containing lysylendopeptidase was added to the gel piece to perform a treatment at 35° C. for 20 hours. After that, the whole solution was subjected to reversed-phase HPLC to separate fragment peptides. As a control, a part of the gel containing no spot was cut out and treated in the same way as described above.

[Reverse-Phase HPLC Conditions]

Column: TSKgel ODS-80Ts (2.0×250 mm, TOSOH),

Solvent A: 0.1% trifluoroacetic acid, 2% acetonitrile,

Solvent B: 0.1% trifluoroacetic acid, 90% acetonitrile,

Flow rate: 200 μl/min,

Temperature: room temperature,

Detection: 210 nm, 280 nm,

Gradient:

TABLE 1

| (minutes) | (% B) |
|---|---|
| 0 | 0 |
| 2 | 0 |
| 7 | 10 |
| 82 | 50 |
| 87 | 100 |
| 92 | 100 |
| 97 | 0 |

Fractionation: 200 μl/Fraction.

For five peaks which were obtained by the reverse-phase HPLC and were considered to be derived from Spot 1, amino acid sequence analyses were performed using Precise 494 HT Protein Sequence System (Applied Biosystems). As a result, the amino acid sequences shown in SEQ ID NOS: 1 to 5 were obtained. The amino acid sequences were subjected to homology search by BLAST search and were found to have high homology to internal sequences of a variety of aldehyde dehydrogenases.

In order to determine the sequence of the gene encoding the protein of Spot 1 induced by acetone, aceA-1F (SEQ ID NO: 6) was created as a degenerate primer based on a fractionated peptide sequence GQYFENPTPITG (SEQ ID NO: 1), and aceA-1R (SEQ ID NO: 7) was created as a degenerate primer based on a peptide sequence MLDHYQQTK (SEQ ID NO: 2). Next, the two kinds of primers were used to perform PCR reactions using a chromosomal DNA of *Pseudonocardia autotrophica* strain NBRC12743 as a template. The PCR reactions were performed using KODplus (TOYOBO CO., LTD.) and the PCR amplification device (Biometra, T Gradient) by repeating a three-step reaction including: denaturation at 98° C. for 20 seconds; annealing at 55° C. for 30 seconds; and elongation at 68° C. for 2 minutes, 25 times. As a result, DNA fragment-4 with a size of about 1.3 kb was amplified. Unless otherwise specified, the following PCR was performed under the above-mentioned conditions. The PCR reaction solution was subjected to agarose gel electrophoresis, and a DNA fragment of about 1.3 kb was cut out and collected by Wizard SV Gel and PCR Clean-Up System (Promega KK.). The DNA fragment-4 was phosphorylated using BKL kit (TAKARA BIO INC.) and ligated to pBluescript II (Stratagene Corporation), which had been digested with EcoRV and dephosphorylated with Calf intestine alkalinephosphatase (New England Biolabs). *Escherichia coli* strain DH5α was transformed with the ligation solution. After that, *Escherichia coli* strain transformed with the plasmid integrated with DNA fragment-4 was selected on LB agar medium (1.5% agar) containing ampicillin (50 μg/ml), X-gal (5-Bromo-4-chloro-3-indolyl-β-D-galactoside; 40 μg/ml)), and IPTG (Isopropyl-β-thiogalactopyranoside; 0.1 mM). Colonies of the *Escherichia coli* were cultured in LB medium containing ampicillin (50 μg/ml), and the plasmid DNA was purified from the proliferated transformed *Escherichia coli* using Wizard Plus SV Minipreps DNA Purification system (Promega KK.). The sequence of the DNA was analyzed by a dye-terminator cycle sequencing method using the resultant plasmid as a template by a DNA base sequence analyzer (Applied Biosystems; 3130) using two kinds of primers (SEQ ID NOS: 8 and 9) according to the accompanying protocol.

Based on the resultant sequence, primers for inverse PCR, aceA-inv-1F (SEQ ID NO: 10) and aceA-inv-1R (SEQ ID NO: 11), were created. Further, a chromosomal DNA of *Pseudonocardia autotrophica* strain NBRC12743 was digested with ClaI, and a self-circularized product was prepared as a template. The inverse PCR reactions were performed using KOD plus (TOYOBO CO., LTD.) and the PCR amplification device (Biometra, T Gradient) by repeating a three-step reaction including: denaturation at 94° C. for 1 minute; annealing at 65° C. for 30 seconds; and elongation at 72° C. for 3 minutes, 30 times. As a result, DNA fragment-5 with a size of about 2.0 kb was amplified. The PCR reaction solution was subjected to agarose gel electrophoresis, and a DNA fragment of about 2.0 kb was cut out to collect DNA fragment-5 by Wizard SV Gel and PCR Clean-Up System (Promega KK.). The DNA fragment-5 was phosphorylated using BKL kit (TAKARA BIO INC.) and ligated to pBluescript II (Stratagene Corporation), which had been digested with EcoRV and dephosphorylated with Calf intestine alkalinephosphatase (New England Biolabs) *Escherichia coli* strain DH5α was transformed with the ligation solution. After that, *Escherichia coli* strain transformed with the plasmid integrated with the DNA fragment-5 was selected on LB agar medium (1.5% agar) containing ampicillin (50 μg/ml), X-gal (40 μg/ml), and IPTG (0.1 mM). Colonies of the *Escherichia coli* were cultured in LB medium containing ampicillin (50 μg/ml), and the plasmid DNA was purified from the proliferated transformed *Escherichia coli* using Wizard Plus SV Minipreps DNA Purification system (Promega KK.). The sequence of the DNA was analyzed by a dye-terminator cycle sequencing method using the resultant plasmid as a template by a DNA base sequence analyzer (Applied Biosystems; 3130) using two kinds of primers (SEQ ID NOS: 8 and 9) according to the accompanying protocol. As a result, an analysis of the upstream part of a gene encoding an acetone-inducible protein (AceA) was achieved.

Based on the resultant sequence, primers for inverse PCR, aceA-inv-2F (SEQ ID NO: 13) and aceA-inv-2R (SEQ ID NO: 14) were created. Further, a chromosomal DNA of *Pseudonocardia autotrophica* strain NBRC12743 was digested with AatII, and a self-circularized product was prepared as a template. Inverse PCR reactions were performed using KOD plus (TOYOBO CO., LTD.) and the PCR amplification device (Biometra, T Gradient) under the same conditions as those in the above-mentioned inverse PCR. As a result, DNA fragment-6 with a size of about 1.0 kb was amplified. The sequence of the DNA fragment-6 was analyzed by the same procedure as described above. As a result, the sequence of the upstream part of the gene encoding the acetone-inducible protein (AceA) was obtained.

Figure 4:
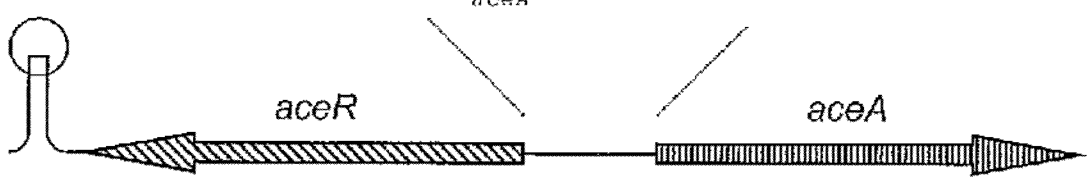
FIG. 4 is a gene map showing a sequence of a region from an aceR gene to an aceA gene (AceR-Pace-AceA; SEQ ID NO: 27).

Based on the resultant sequence, primers for inverse PCR, aceA-inv-3F (SEQ ID NO: 15) and aceA-inv-3R (SEQ ID NO: 16), were created. Further, a chromosomal DNA of *Pseudonocardia autotrophica* strain NBRC12743 was digested with BamHI, and a self-circularized product was prepared as a template. Inverse PCR reactions were performed using KOD plus (TOYOBO CO., LTD.) and the PCR amplification device (Biometra, T Gradient) under the same conditions as those in the above-mentioned inverse PCR. As a result, DNA fragment-7 with a size of about 3.0 kb was amplified. The sequence of the DNA fragment-7 was analyzed by the same procedure as described above. As a result, an analysis of the upstream part of the gene encoding the acetone-inducible protein (AceA) was achieved (SEQ ID NO: 48). The plasmid used as the template for the analysis was considered to include an unanalyzed part of the upstream of the aceA gene, and hence a sequence analysis was performed by the primer walking method to determine the DNA sequence of the open reading frame of a protein (AceR) present in the reverse direction to the upstream of the aceA gene and the sequence to the stem-loop structure present on the downstream of aceR (FIG. 4, SEQ ID NO: 47). The results suggested that the promoter region for expression of aceA was present between the aceA gene and the aceR gene, and hence a sequence of about 0.45 kb (Pace; SEQ ID NO: 26) was used as an acetone-inducible promoter region for the following vector construction. It should be noted that BLAST search using the amino acid sequence of AceR showed that the sequence had homology to GAF sensor protein and a transcriptional regulator (M. Y. Galperin, Environ. Microbial., 6(6), 552-567 (2004)). Thus, the sequence of the region from the aceR gene to the aceA gene (AceR-Pace-AceA; SEQ ID NO: 27) shown in FIG. 4 was determined.

(4) Construction of Acetone-Inducible Expression Vector Capable of Transforming *Pseudonocardia autotrophica* (Construction of VDH-Expressing Vector)

Figure 5:
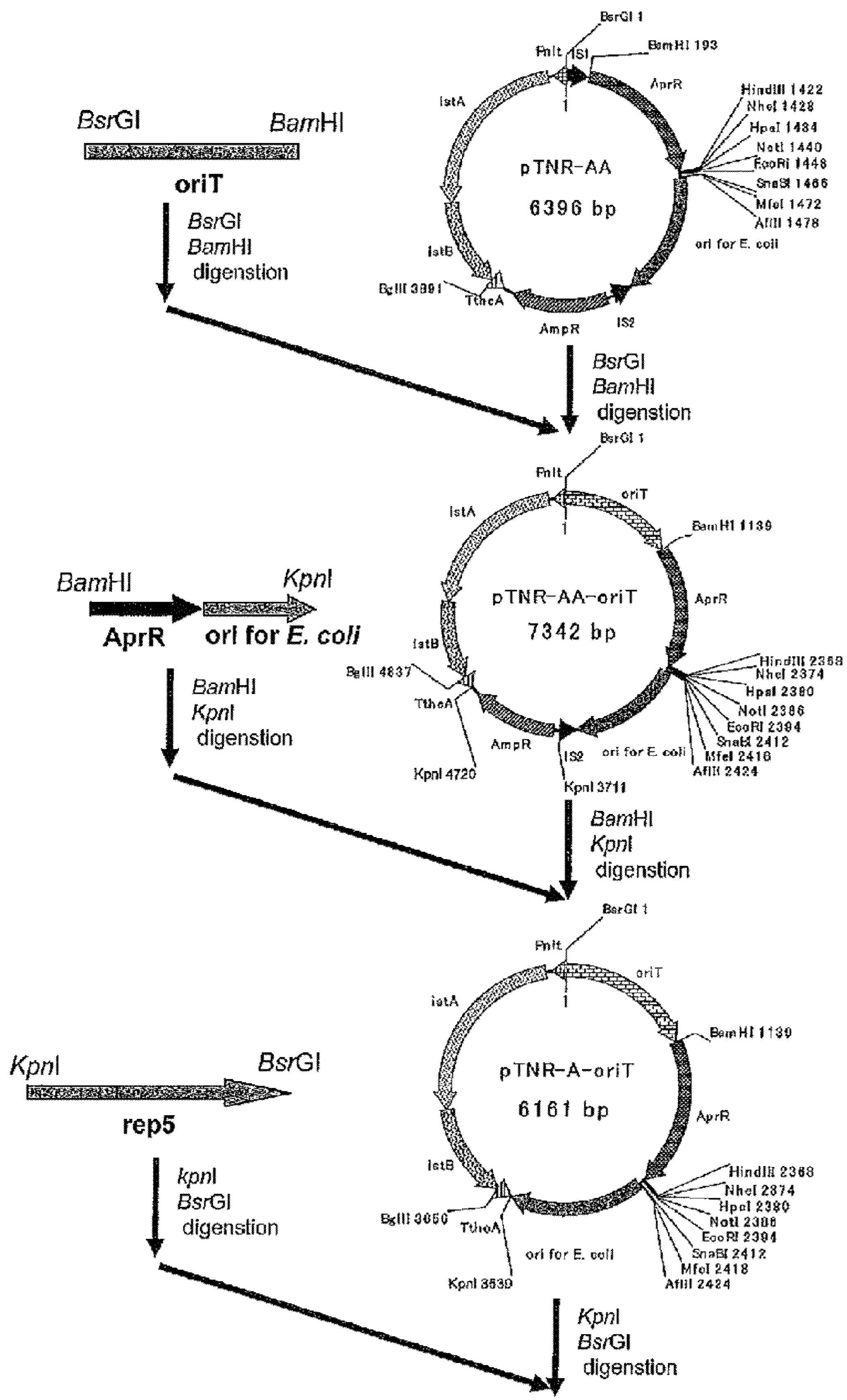
FIG. 5A is a diagram illustrating construction of VDH expression vectors.
FIG. 5B continues from FIG. 5A.
Figure 5:
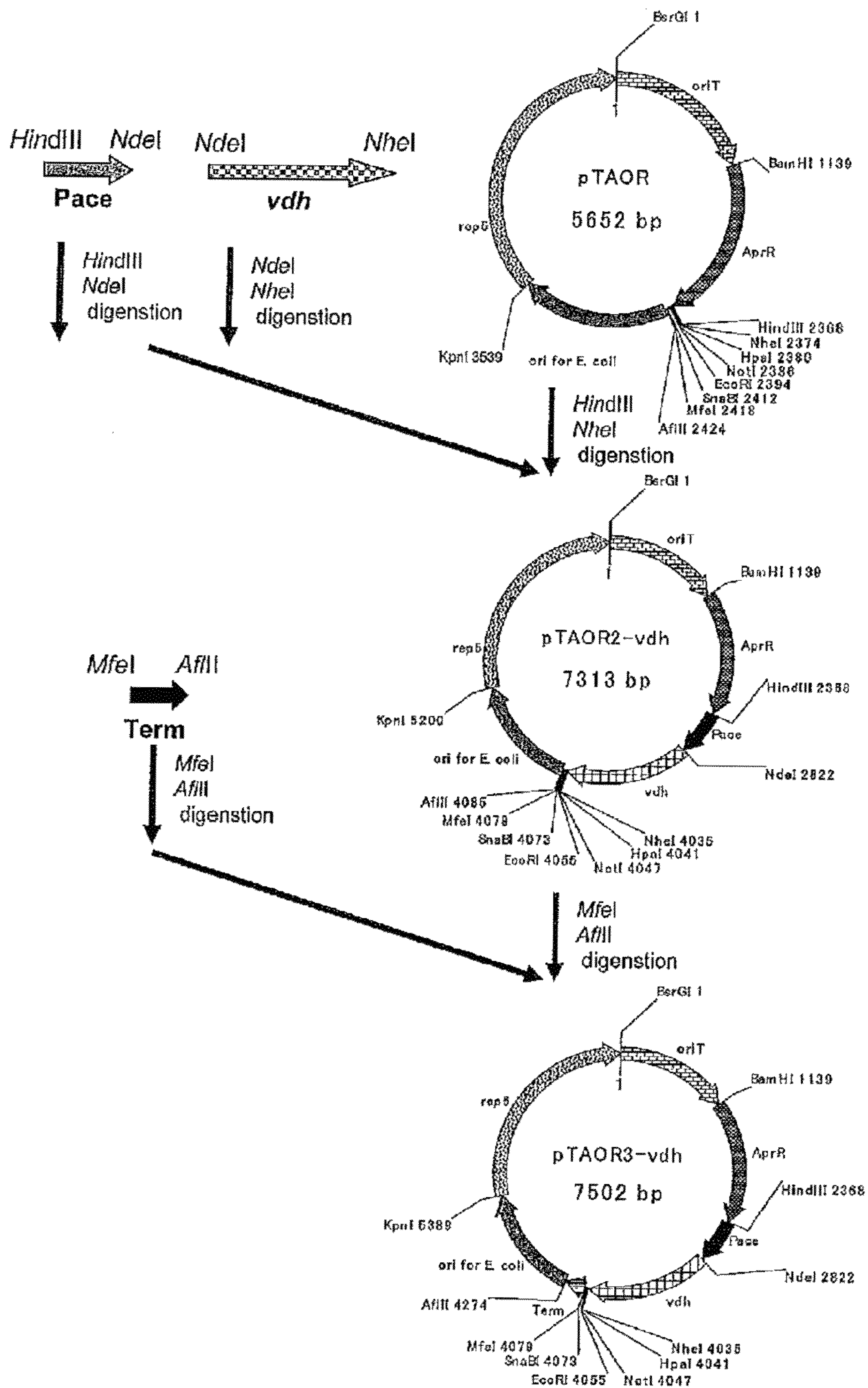

In order to amplify the oriT gene, primers oriT-1F (SEQ ID NO: 28) and oriT-1R (SEQ ID NO: 29) were created. The primers were used to perform PCR reactions using pTNR-oriT (K. I. Sallam, Gene, 386, 173-182 (2007)) as a template. As a result, a DNA fragment with a length of about 1.1 kb was amplified. The DNA fragment was digested with BsrGI and BamHI and subjected to agarose gel electrophoresis, and a DNA fragment of about 1.1 kb was cut out and collected by Wizard SV Gel and PCR Clean-Up System (Promega KK.), to thereby obtain DNA fragment-8. A plasmid pTNR-AA (Tamura Tomohiro, et al., Journal of Environmental Biotechnology, 7(1), 3-10, 2007) was digested with BsrGI and BamHI and subjected to agarose gel electrophoresis, and a DNA fragment of about 6.2 kb was cut out and collected by Wizard SV Gel and PCR Clean-Up System (Promega KK.), to thereby obtain DNA fragment-9. The DNA fragment-9 and DNA fragment-8 were ligated using DNA Ligation kit ver 2.1 (TAKARA BIO INC.), to thereby obtain pTNR-AA-oriT (FIG. 5).

Subsequently, the following procedure was performed to remove an ampicillin-resistant gene from pTNR-AA-oriT. In order to amplify an apramycin-resistant gene of pTNR-AA and an essential region for replication of pTNR-AA in *Escherichia coli*, primers pTNR-AA-apr-1F (SEQ ID NO: 30) and pTNR-AA-ori-1R (SEQ ID NO: 31) were created. The primers were used to perform PCR reactions using pTNR-AA as a template. The PCR reactions were performed using KOD plus (TOYOBO CO., LTD.) and the PCR amplification device (Biometra, T Gradient) by repeating a three-step reaction including: denaturation at 98° C. for 20 seconds; annealing at 55° C. for 30 seconds; and elongation at 68° C. for 3 minutes, 25 times. As a result, a DNA fragment with a length of about 2.4 kb was amplified. The DNA fragment was digested with BamHI and KpnI and subjected to agarose gel electrophoresis, and a DNA fragment of about 2.4 kb was cut out and collected by Wizard SV Gel and PCR Clean-Up System (Promega KK.), to thereby obtain DNA fragment-10. A plasmid pTNR-AA-oriT was digested with BamHI and KpnI and subjected to agarose gel electrophoresis, and a DNA fragment of about 3.7 kb was cut out and collected by Wizard SV Gel and PCR Clean-Up System (Promega KK.), to thereby obtain DNA fragment-11. The DNA fragment-11 and DNA fragment-10 were ligated using DNA Ligation kit ver 2.1 (TAKARA BIO INC.), to thereby obtain pTNR-A-oriT (FIG. 5).

Next, the following procedure was performed to remove the istAB gene of pTNR-A-oriT and to insert the essential region for replication in *Pseudonocardia autotrophica* (rep5)

identified in Production Example (2) into the site. In order to amplify the essential region for replication of pPA43082 (rep5), primers rep-4F (SEQ ID NO: 32) and rep-6R (SEQ ID NO: 25) were created. The primers were used to perform PCR reactions using pPA43082 as a template. The PCR reactions were performed using KOD plus (TOYOBO CO., LTD.) and the PCR amplification device (Biometra, T Gradient) by repeating a three-step reaction including: denaturation at 98° C. for 20 seconds; annealing at 55° C. for 30 seconds; and elongation at 68° C. for 3 minutes, 25 times. As a result, a DNA fragment with a length of about 2.1 kb was amplified. The DNA fragment was digested with BsrGI and KpnI and subjected to agarose gel electrophoresis, and a DNA fragment of about 2.1 kb was cut out and collected by Wizard SV Gel and PCR Clean-Up System (Promega KK.), to thereby obtain DNA fragment-12. A plasmid pTNR-A-oriT was digested with BsrGI and KpnI and subjected to agarose gel electrophoresis, and a DNA fragment of about 3.5 kb was cut out and collected by Wizard SV Gel and PCR Clean-Up System (Promega KK.), to thereby obtain DNA fragment-13. The DNA fragment-13 and DNA fragment-12 were ligated using DNA Ligation kit ver 2.1 (TAKARA BIO INC.), to thereby obtain pTAOR (FIG. 5).

Next, the following procedure was performed to insert the acetone-inducible promoter sequence and vdh gene (SEQ ID NO: 44) into the multicloning site of pTAOR (WO 2008/096695 A1). First, in order to amplify the acetone-inducible promoter sequence, primers Pace-HindIII-1F (SEQ ID NO: 33) and Pace-NdeI-1R (SEQ ID NO: 34) were created. The primers were used to perform PCR reactions using a genomic DNA of *Pseudonocardia autotrophica* as a template. The PCR reactions were performed using KOD plus (TOYOBO CO., LTD.) and the PCR amplification device (Biometra, T Gradient) by repeating a three-step reaction including: denaturation at 98° C. for 20 seconds; annealing at 55° C. for 30 seconds; and elongation at 68° C. for 1 minute, 25 times. As a result, a DNA fragment with a length of about 0.4 kb was amplified. The DNA fragment was digested with HindIII and Ndel and subjected to agarose gel electrophoresis, and a DNA fragment of about 0.4 kb was cut out and collected by Wizard SV Gel and PCR Clean-Up System (Promega KK.), to thereby obtain DNA fragment-14. Subsequently, in order to amplify the vdh gene, primers VDH-1F (SEQ ID NO: 35) and VDH-1R (SEQ ID NO: 36) were created. The primers were used to perform PCR reactions using the genomic DNA of *Pseudonocardia autotrophica* NBRC12743 as a template. As a result, a DNA fragment with a length of about 1.2 kb was amplified. The DNA fragment was digested with Ndel and Nhel and subjected to agarose gel electrophoresis, and a DNA fragment of about 1.2 kb was cut out and collected by Wizard SV Gel and PCR Clean-Up System (Promega KK.), to thereby obtain DNA fragment-15. AplasmidpTAOR was digested with HindIII and Nhel and subjected to agarose gel electrophoresis, and a DNA fragment of about 5.7 kb was cut out and collected by Wizard SV Gel and PCR Clean-Up System (Promega KK.), to thereby obtain DNA fragment-16. The DNA fragment-16, DNA fragm$^{-}$ used to perform PCR reactions using pTipQT2 as a template. The PCR reactions were performed using KOD plus (TOYOBO CO., LTD.) and the PCR amplification device (Biometra, T Gradient) by repeating a three-step reaction including: denaturation at 98° C. for 20 seconds; annealing at 55° C. for 30 seconds; and elongation at 68° C. for 1 minute, 25 times. As a result, a DNA fragment with a length of about 0.2 kb was amplified. The DNA fragment was digested with MfeI and AflII and subjected to agarose gel electrophoresis, and a DNA fragment of about 0.2 kb was cut out and collected by Wizard SV Gel and PCR Clean-Up System (Promega KK.), to thereby obtain DNA fragment-17. The plasmid pTAOR2-vdh was digested with MfeI and AflII and subjected to agarose gel electrophoresis, and a DNA fragment of about 7.3 kb was cut out and collected by Wizard SV Gel and PCR Clean-Up System (Promega), to thereby obtain DNA fragment-18. The DNA fragment-18 and DNA fragment-17 were ligated using DNA Ligation kit ver 2.1 (TAKARA BIO INC.), to thereby obtain an acetone-inducible VDH-expressing vector, pTAOR3-vdh (SEQ ID NO: 45) (FIG. 5).

(5) Construction of BoxAB Expression Vector

Genes of boxA and boxB (hereinafter, also referred to as boxAB genes) derived from *Streptomyces* sp. TM-7 was acquired as a gene of an enzyme which catalyzes hydroxylation of compactin into pravastatin by Tadashi Fujii et al. (WO 2002/099109 A1). It should be noted that *Streptomyces* sp. strain TM-7 is a strain isolated by MERCIAN CORPORATION and has been domestically deposited with International Patent Organism Depositary, National Institute of Advanced Industrial Science and Technology (Central 6, 1-1-1, Higashi, Tsukuba, Ibaraki 305-8566, Japan) (FERM P-18312) on Apr. 25, 2001 and transmitted to an international depositary authority on Apr. 5, 2002 (FERM BP-8003). The place of sampling is soil in the Fujisawa factory of MERCIAN CORPORATION at Johnan, Fujisawa, Kanagawa, Japan, and the date of sampling, isolation source, isolator, and date of isolation are unknown.

In order to construct an acetone-inducible BoxAB expression vector of *Pseudonocardia autotrophica*, the following procedure was performed. First, in order to amplify the boxAB genes, primers BoxAB-1F (SEQ ID NO: 39) and BoxAB-1R (SEQ ID NO: 40) were created. The primers were used to perform PCR reactions using *Streptomyces* sp. TM-7 as a template. As a result, a DNA fragment with a length of about 1.5 kb was amplified. The DNA fragment was digested with NdeI and SpeI and subjected to agarose gel electrophoresis, and a DNA fragment of about 1.5 kb was cut out and collected by Wizard SV Gel and PCR Clean-Up System (Promega KK.), to thereby obtain DNA fragment-19. A plasmid pTAOR3-vdh was digested with NdeI and SpeI and subjected to agarose gel electrophoresis, and a DNA fragment of about 6.3 kb was cut out and collected by Wizard SV Gel and PCR Clean-Up System (Promega KK.), to thereby obtain DNA fragment-20. The DNA fragment-20 and DNA fragment-19 were ligated using DNA Ligation kit ver 2.1 (TAKARA BIO INC.), to thereby obtain an acetone-inducible BoxAB expression vector, pTAOR3-boxAB (FIG. 6). According to the method shown in Production Example (6) described below, *Pseudonocardia autotrophica* was tried to be transformed with pTAOR3-boxAB, but no transformed strain was able to be obtained. Therefore, the structure of the BoxAB expression vector was changed by the following procedure.

First, in order to amplify the acetone-inducible promoter sequence, boxAB genes, and terminator sequence, primers PBT-1F (SEQ ID NO: 41) and PBT-1R (SEQ ID NO: 42) were created. The primers were used to perform PCR reactions using pTAOR3-boxAB as a template. As a result, a DNA fragment with a length of about 2.0 kb was amplified. The DNA fragment was digested with KpnI and subjected to agarose gel electrophoresis, and a DNA fragment of about 2.0 kb was cut out and collected by Wizard SV Gel and PCR Clean-Up System (Promega KK.), to thereby obtain DNA fragment-21. Subsequently, in order to remove the promoter sequence, boxAB genes, and terminator sequence from the plasmid pTAOR3-boxAB, the fragment was digested with HindIII and AflII and subjected to agarose gel electrophoresis, and a DNA fragment of about 5.6 kb was cut out and collected by Wizard SV Gel and PCR Clean-Up System (Promega KK.), to thereby obtain DNA fragment-22. End blunting and self-ligation of the DNA fragment-22 were performed by BKL kit (TAKARA BIO INC.), to thereby obtain pTAOR4. The plasmid pTAOR4 was digested with KpnI and subjected to agarose gel electrophoresis, and a DNA fragment of about 5.6 kb was cut out and collected by Wizard SV Gel and PCR Clean-Up System (Promega KK.), to thereby obtain DNA fragment-23. The DNA fragment-23 was dephosphorylated with alkaline phosphatase (Calf intestine) (TAKARA BIO INC.) and collected by Wizard SV Gel and PCR Clean-Up System (Promega KK), to thereby obtain DNA fragment-24. *Escherichia coli* DH5α was transformed with a reaction solution in which the DNA fragment-21 and DNA fragment-24 had been ligated using DNA Ligation kit ver 2.1 (TAKARA BIO INC.), and colonies of transformed strains were obtained on LB agar medium containing 60 μg/ml apramycin. Eight colonies of the resultant colonies were arbitrarily selected and cultured in 2 ml of LB medium containing 60 μg/ml apramycin, and the plasmid DNA was purified from the proliferated transformed *Escherichia coli* by Wizard Plus SV Minipreps DNA Purification system (Promega KK.). Analyses were performed by the dye-terminator cycle sequencing method using the resultant eight samples of plasmids as templates by the DNA base sequence analyzer (Applied Biosystems; 3130) using a primer (SEQ ID NO: 43) according to the accompanying protocol. The results showed that plasmids pTAOR4-For-boxAB and pTAOR4-Rev-boxAB (SEQ ID NO: 46), into which the DNA fragment-21 was inserted in the reverse directions, were obtained (FIG. 6).

(6) Transformation of *Pseudonocardia autotrophica* with VDH and BoxAB Expression Vector In order to transform *Pseudonocardia autotrophica* strain NBRC12743 with pTAOR3-vdh, pTAOR3-boxAB, pTAOR4-For-boxAB, and pTAOR4-Rev-boxAB created in Production Example (4) and Production Example (5) by a conjugation method, the following procedure was performed. First, *Escherichia coli* strain S17-1 was transformed with the respective plasmids. The resultant transformed strains were cultured in LB medium containing 60 μg/ml apramycin at 30° C. for 15 hours to prepare culture media. On the other hand, *Pseudonocardia autotrophica* strain NBRC12743 was cultured in LB medium at 30° C. for 72 hours to prepare a culture medium. 200 μl of each of the culture media of the *Escherichia coli* strain S17-1 were centrifuged at 7,000 rpm for 30 seconds to precipitate bacterial cells. The supernatant was discarded, and 200 μl of LB medium was newly added to suspend the bacterial cells. 500 μl of the culture medium of *Pseudonocardia autotrophica* strain NBRC12743 were added thereto, and the suspension was mixed. The suspension was centrifuged at 7,000 rpm for 30 seconds to precipitate the bacterial cells. 500 μl of the supernatant was discarded, and the bacterial cells were suspended in 200 μl of the residual supernatant. 150 μl of the cell suspension was spread to LB agar medium, and the cells were cultured at 30° C. for 24 hours. Growth of the bacterial cells on the surface of the agar medium was confirmed, and 2 ml of LB medium was added, followed by suspension of the bacterial cells using a spreader. 200 μl of the cell suspension was spread to LB agar medium containing 24 μg/ml apramycin and 50 μg/ml nalidixic acid, and the cells were cultured at 30° C. for 7 days, to thereby obtain only transformants of *Pseudonocardia autotrophica* strain NBRC12743 transformed with the plasmids pTAOR3-vdh and pTAOR4-Rev-boxAB.

(7) Protein Expression Test Using Transformed Strain of *Pseudonocardia autotrophica* NBRC12743

1) VDH Expression Test

VDH is an enzyme protein belonging to cytochrome P450 group. Cytochrome P450 is a collective term of a group of proteins which are protoheme-containing proteins and show a characteristic absorbance peak at about 450 nm when carbon monoxide is bonded to reduced heme iron. Therefore, if a vdh gene is highly expressed in a transformed strain, expression of the gene can be detected by a carbon monoxide-binding spectrum analysis.

Figure 7:
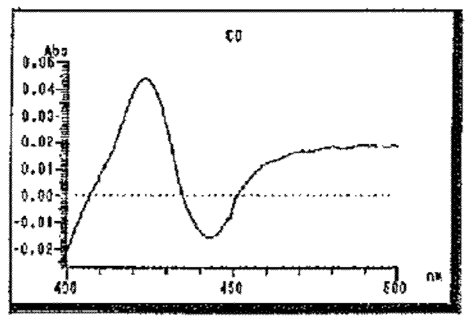
FIG. 7 is graphs showing the results of a VDH expression test by a reduced carbon monoxide-binding spectrum analysis.
Figure 7:
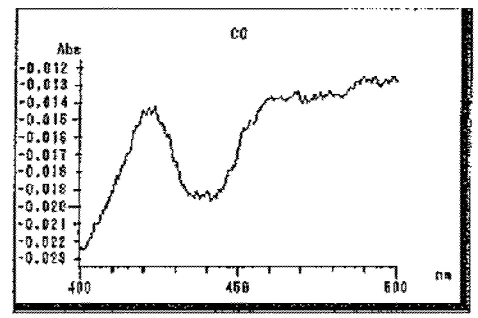
Figure 7:
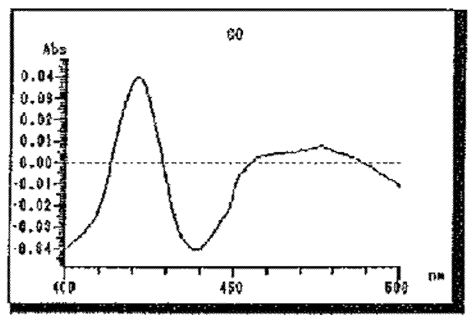
Figure 7:
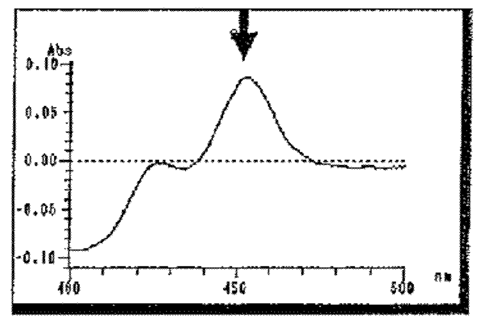

A test for confirming expression in VDH-inducible bacterial cells was performed by the following procedure. Colonies of *Pseudonocardia autotrophica* NBRC12743 transformed with pTAOR3-vdh obtained in Production Example (6) (*P. autotrophica* NBRC12743/pTAOR3-vdh) were inoculated into 100 ml of a preculture medium (1.5% glucose, 0.3% yeast extract, 0.4% sodium chloride, 0.2% calcium carbonate, and 1.5% polypeptone) containing 24 μg/ml apramycin and cultured at 30° C. and 220 rpm for 72 hours. As controls, *Pseudonocardia autotrophica* NBRC12743 wild-type strain and *Pseudonocardia autotrophica* NBRC12743 strain transformed with pTAOR were cultured in the same way as described above. 1 ml of each of the culture media was inoculated into 100 ml of a main culture medium (1% polypeptone, 2% glucose, 1% SOYPRO, 0.5% yeast extract, 0.04% $K_2HPO_4$, 0.04% sodium chloride, and 0.3% calcium carbonate) containing 24 μg/ml apramycin. The cells were cultured at 30° C. and 220 rpm for 48 hours, and 1 ml of acetone (final concentration: 1%) was added thereto, followed by culture at 30° C. and 220 rpm for 24 hours. *Pseudonocardia autotrophica* strain NBRC12743 transformed with pTAOR3-vdh was further subjected to a test without adding acetone. The culture medium was centrifuged at 7,000 rpm for 10 minutes, to thereby obtain bacterial cells as precipitates. The supernatant was discarded, and CV buffer was added to the culture medium in an amount of one-fifth of the medium, to thereby prepare a five-fold-concentrated cell suspension. A procedure of vigorously shaking 1 ml of the cell suspension using FastPROTEIN BLUE kit (Funakoshi Corporation) by FastPrep FP120 (BIO101, SAVANT) at a speed of 6.0 for 40 seconds was repeated three times while the sample was cooled on ice between the procedures, to thereby break the cells. The broken cell suspension was centrifuged at 13,000 rpm for 10 minutes, to thereby obtain a cell-free extract in the supernatant. The cell-free extract was divided into two test tubes with a cap in an amount of 700 μl, and carbon monoxide was passed through one of the cell-free extract. Next, sodium hydrosulfite was added to both the cell-free extracts in a small amount. The absorption spectrum from 400 nm to 500 nm of the sample through which carbon monoxide was not passed was defined as a baseline, and absorption from 400 nm to 500 nm of the sample through which carbon monoxide was passed was scanned using a spectrophotometer (U-3310 SpectrophotoMeter, HITACHI, Ltd.). As a result, an absorption peak characteristic to cytochrome P450 was observed at about 450 nm, and a VDH expression level in the culture medium was calculated from the absorption based on the molecular extinction coefficient of carbon monoxide-bonded and reduced P450, defined as 91 per mM. The results of the calculation suggested that 202 nM VDH was expressed per culture medium (FIG. 7).

2) BoxAB Expression Test

Figure 8:
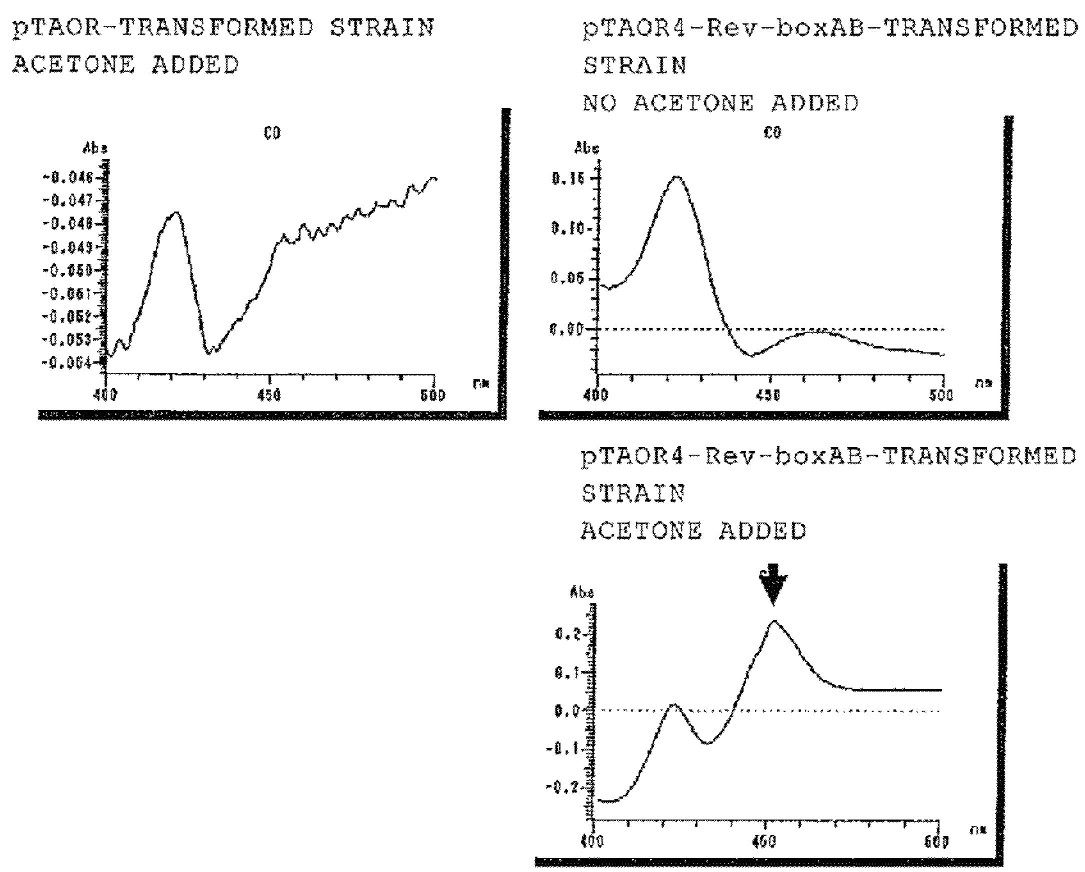
FIG. 8 is graphs showing the results of a BoxA expression test by a reduced carbon monoxide-binding spectrum analysis.

The boxAB genes derived from *Streptomyces* sp. TM-7 were acquired as a gene of an enzyme which catalyzes hydroxylation of compactin into pravastatin by Tadashi Fujii et al. (WO 2002/099109 A1). BoxA is cytochrome P450, and if the gene is highly expressed, expression of the gene can be detected by the carbon monoxide-binding spectrum analysis. In addition, a conversion test of compactin into pravastatin by BoxAB-inducible bacterial cells can confirm whether the gene is expressed and functions. Colonies of *Pseudonocardia autotrophica* NBRC12743 transformed with pTAOR4-Rev-boxAB obtained in Production Example (6) (*P. autotrophica* NBRC12743/pTAOR4-Rev-boxAB) were inoculated into 100 ml of a preculture medium (1.5% glucose, 0.3% yeast extract, 0.4% sodium chloride, 0.2% calcium carbonate, and 1.5% polypeptone) containing 24 μg/ml apramycin and cultured at 30° C. and 220 rpm for 72 hours. As controls, *Pseudonocardia autotrophica* NBRC12743 wild-type strain and *Pseudonocardia autotrophica* NBRC12743 strain transformed with pTAOR were cultured at the same time. 1 ml of each of the culture media was inoculated into 100 ml of a main culture medium (1% polypeptone, 2% glucose, 1% SOYPRO, 0.5% yeast extract, 0.04% $K_2HPO_4$, 0.04% sodium chloride, and 0.3% calcium carbonate) containing 24 μg/ml apramycin. The cells were cultured at 30° C. and 220 rpm for 48 hours, and 1 ml of acetone (final concentration: 1%) was added thereto, followed by culture at 30° C. and 220 rpm for 24 hours. *Pseudonocardia autotrophica* strain NBRC12743 transformed with pTAOR4-Rev-boxAB was further subjected to a test without adding acetone. 50 ml of the culture medium was used for conversion of compactin, and the residual culture medium was centrifuged at 7,000 rpm for 10 minutes, to thereby obtain bacterial cells as precipitates. The supernatant was discarded, and CV buffer was added to the precipitates in an amount of one-fifth of the medium, to thereby prepare a five-fold-concentrated cell suspension. A procedure of vigorously shaking 1 ml of the cell suspension using FastPROTEIN BLUE kit (Funakoshi Corporation) by FastPrep FP120 (BIO101, SAVANT) at a speed of 6.0 for 40 seconds was repeated three times while the sample was cooled on ice between the procedures, to thereby break the cells. The broken cell suspension was centrifuged at 13,000 rpm for 10 minutes, to thereby obtain a cell-free extract in the supernatant. The cell-free extract was divided into two test tubes with a cap in an amount of 700 μl, and carbon monoxide was passed through one of the cell-free extract. Next, sodium hydrosulfite was added to both the cell-free extracts in a small amount. The absorption spectrum from 400 nm to 500 nm of the sample through which carbon monoxide was not passed was defined as a baseline, and absorption from 400 nm to 500 nm of the sample through which carbon monoxide was passed was scanned using a spectrophotometer (U-3310 SpectrophotoMeter, HITACHI, Ltd.). As a result, a clear absorption peak was observed at about 450 nm in the sample of the strain transformed with pTAOR4-Rev-boxAB in the culture medium to which acetone was added, and it was suggested that 396 nM BoxA was expressed per culture medium (FIG. 8).

Example

Production of Pravastatin

Figure 10:
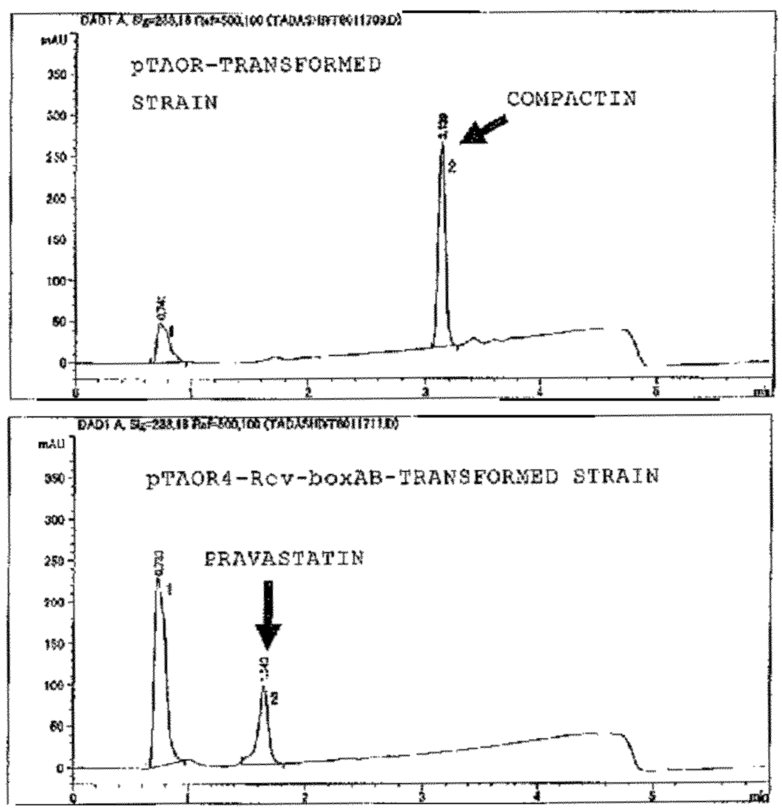
FIG. 10 is graphs showing the results of a compactin production test using a BoxAB-expressing strain.

A pravastatin production test using a BoxAB-expressing strain was performed. Compactin is converted into pravastatin by BoxA (FIG. 9). According to the above-mentioned culture method, the pTAOR4-Rev-boxAB-transformed strain was cultured, and induction by acetone was performed for 24 hours. As a control, a pTAOR-transformed strain was used. The culture medium in which induction was performed by 50 ml of acetone was centrifuged to precipitate the bacterial cells. The cells were suspended in 10 ml of Buffer A (50 mM potassium phosphate buffer, pH 7.4, 2% glycerol) to prepare a five-fold-concentrated cell suspension, and compactin was added thereto at a final concentration of 250 mg/L to perform conversion for 4 hours. A solvent (methanol:acetonitrile=1:1) was added to the sample at a ratio of 1:1 to stop the reaction, and the suspension was centrifuged at 15,000 rpm for 10 minutes to obtain the supernatant as a sample for HPLC analysis. Pravastatin was analyzed by HPLC under the following conditions. FIG. 10 shows the results of the analysis.

[Pravastatin Analyzing Conditions]

Column: Chromolith Performance RP-18e (100×4.6 mm, Merck & Co., Inc.),

Solvent A: water:triethylamine:acetic acid=100:0.1:0.1,

Solvent B: methanol:triethylamine:acetic acid=100:0.1:0.1,

Flow rate: 2.0 ml/min,

Temperature: 40° C.,

Detection: 238 nm,

Gradient:

TABLE 2

| (minutes) | (% B) |
|---|---|
| 0 | 50 |
| 3.0 | 90 |
| 3.5 | 90 |
| 3.51 | 50 |
| 5.0 | 50 |

Injection: 15 μl,

| Retention time: | compactin | 3.1 minutes, |
|---|---|---|
| | pravastatin | 1.6 minutes. |

As is clear from FIG. 10, in the case of the BoxAB-expressing strain, production of 244 mg/L pravastatin was detected. In the case of the controls, production of pravastatin was not confirmed, and the results showed that pravastatin was produced by the reaction of BoxAB.

Figure 11:
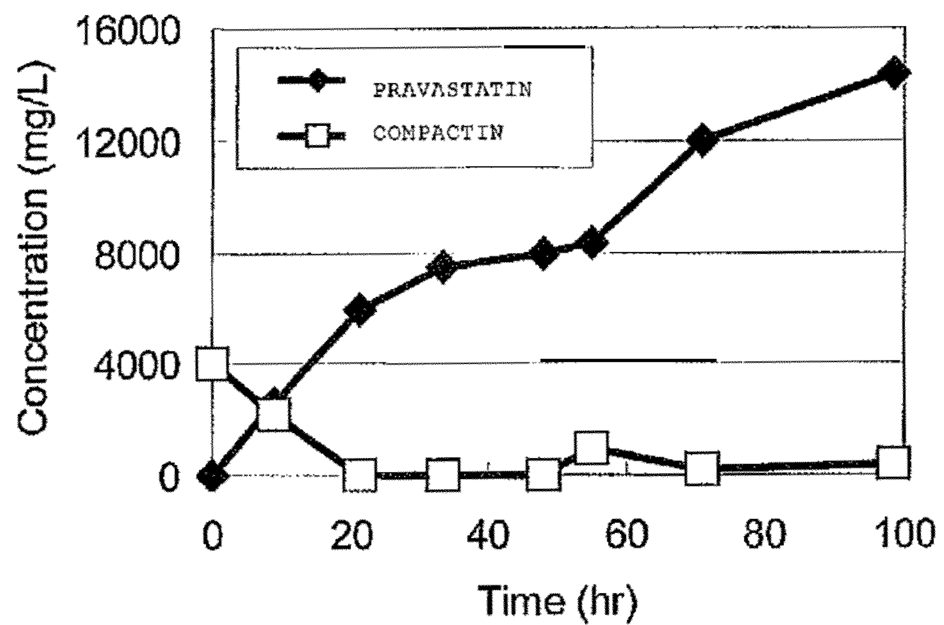
FIG. 11 is a graph showing production of pravastatin.

Compactin (ring-opened form) was fed to the transformed BoxAB expressing strain (*P. autotrophica* NBRC12743/pTAOR4-Rev-boxAB) of *Pseudonocardia autotrophica* NBRC12743, which had been cultured and underwent induction by acetone in the same way as described above, to examine the accumulation of pravastatin. A solution of 25 g/L compactin (ring-opened form) was added to 25 ml of the BoxAB-induced culture medium in an amount of 4 ml at the start of the reaction, in an amount of 1 ml at 9 hours from the start, in an amount of 2 ml at 21.5 hours from the start, in an amount of 2 ml at 33.5 hours from the start, in an amount of 3 ml at 48 hours from the start, in an amount of 3 ml at 55 hours from the start, in an amount of 3 ml at 71 hours from the start, and in an amount of 3 ml at 80 hours from the start. FIG. 11 shows time-dependent conversion of concentrations of compactin and pravastatin in the medium. As the result, 13 g/L pravastatin was accumulated for 100 hours in the conversion solution, and a highly efficient pravastatin production system was constructed.

The invention claimed is:

1. An expression vector, including a replication initiation region derived from *Pseudonocardia autotrophica*, a multicloning site for introducing an exogenous gene, an exogenous gene introduced into the multicloning site, a promoter, a terminator, and a defective selection marker, which autonomously replicates in cells of *Pseudonocardia autotrophica* to enable expression of the exogenous gene introduced, wherein the replication initiation region comprises a base sequence represented by SEQ ID NO: 49, a base sequence complementary to the entire base sequence represented by SEQ ID NO: 49, a base sequence having 90% or more homology to SEQ ID NO: 49, or a base sequence complementary to the entire base sequence having 90% or more homology to SEQ ID NO: 49.

2. The expression vector according to claim 1, in which the promoter is induced by acetone to express the exogenous gene.

3. The expression vector according to claim 2, in which the promoter region comprises a base sequence represented by SEQ ID NO: 26 or a base sequence having 90% or more homology to the above base sequence or a complementary sequence thereof.

4. The expression vector according to claim 1, further including a replication initiation region derived from *Escherichia coli*, and being autonomously replicable in both *Pseudonocardia autotrophica* and *Escherichia coli*, and can be used as a shuttle vector.

5. The expression vector according to claim 4, further comprising an oriT region and which can perform transformation by conjugation of *Escherichia coli* S17-1 and *Pseudonocardia autotrophica*.

6. The expression vector according to claim 1, in which the exogenous gene is a gene encoding vitamin D hydroxylase or a gene encoding compactin hydroxylase.

7. A transformant of *Pseudonocardia autotrophica* having introduced thereinto the expression vector according to claim 1.

8. A method of producing a protein comprising: introducing the expression vector according to claim 1 into *Pseudonocardia autotrophica* to be transformed; and expressing the exogenous gene in the resultant transformant to produce a protein.

9. A method of producing 25-hydroxyvitamin D2, 25-hydroxyvitamin D3, or an active form of vitamin D including: transforming *Pseudonocardia autotrophica* with the expression vector according to claim 1, having introduced thereinto a vitamin D hydroxylase gene as an exogenous gene; inducing expression of vitamin D hydroxylase from the resultant transformant; and culturing the transformant with vitamin D group, thereby producing 25-hydroxyvitamin D2, 25-hydroxyvitamin D3, or an active form of the vitamin D group.

10. The method of producing an active form of vitamin D according to claim 9, in which the active form of vitamin D is 1α,25-dihydroxyvitamin D3.

11. A method of producing pravastatin including: transforming *Pseudonocardia autotrophica* with the expression vector according to claim 1, having introduced thereinto a compactin hydroxylase gene as an exogenous gene; inducing expression of compactin hydroxylase from the resultant transformant; and culturing the transformant with compactin, thereby producing pravastatin from compactin.

12. The expression vector according to claim 1, wherein the replication initiation region is selected from the group consisting of rep1 and rep5.

13. The expression vector according to claim 1, wherein the promoter is selected from the group consisting of an acetone-inducible promoter, a thiostrepton-inducible promoter, and an ermE promoter.

14. The expression vector according to claim 1, wherein the vector is selected from the group consisting of pTAOR3-vdh, pTAOR4-For-boxAB and pTAOR4-Rev-boxAB.

* * * * *

SEQUENCE LISTING

<160> NUMBER OF SEQ ID NOS: 51

<210> SEQ ID NO 1
<211> LENGTH: 12
<212> TYPE: PRT
<213> ORGANISM: Pseudonocardia autotrophica

<400> SEQUENCE: 1

Gly Gln Tyr Phe Glu Asn Pro Thr Pro Ile Thr Gly
1 5 10

<210> SEQ ID NO 2
<211> LENGTH: 9
<212> TYPE: PRT
<213> ORGANISM: Pseudonocardia autotrophica

<400> SEQUENCE: 2

Met Leu Asp His Tyr Gln Gln Thr Lys
1 5

<210> SEQ ID NO 3
<211> LENGTH: 14
<212> TYPE: PRT
<213> ORGANISM: Pseudonocardia autotrophica

<400> SEQUENCE: 3

Ala Leu Asp Ala Ala His Gly Ala Ala Pro Ala Trp Gly Lys
1 5 10

<210> SEQ ID NO 4
<211> LENGTH: 19
<212> TYPE: PRT
<213> ORGANISM: Pseudonocardia autotrophica

<400> SEQUENCE: 4

Ser Pro Asn Ile Phe Phe Asp Asp Val Ala Ser Gln Gln Asp Ala Phe
1 5 10 15

Tyr Asp Lys

<210> SEQ ID NO 5
<211> LENGTH: 16
<212> TYPE: PRT
<213> ORGANISM: Pseudonocardia autotrophica

<400> SEQUENCE: 5

Met Ala Asp Arg Ile Glu Ala Asn Leu Glu Ala Val Ala Ile Ala Glu
1 5 10 15

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
ggscartayt tygaraaycc 20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:

<221> NAME/KEY: misc_feature
<222> LOCATION: (15)..(15)
<223> OTHER INFORMATION: n is a, c, g, or t

<400> SEQUENCE: 7
tgctgrtart grtcnarcat 20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
taatacgact cactataggg 20

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
attaaccctc actaaaggga a 21

<210> SEQ ID NO 10
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 10
cggatcgagg cgaacctcga ggcggtcgcg 30

<210> SEQ ID NO 11
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 11
gtcggccatc ttgttcagga tgttcgcccg 30

<210> SEQ ID NO 12
<211> LENGTH: 8047
<212> TYPE: DNA
<213> ORGANISM: Pseudonocardia autotrophica

<400> SEQUENCE: 12
actcctcgat cagctcggac agcacggtct cgtagtcgcc caggtcttct ggcgcggtgc 60
ctcgggagac ggcgaactcg atgaggtgcc gcacgtgggc agtcatcgtc gggatctcct 120
gctgctcggc ccacgcccgc gcctcgcctg cggacttcca ccggctgtcg acgtcgacca 180
ggagcagcgc cgcggtcagc ggcgacaggg cgtcggcctc ggccgcgagc tcaaagaccc 240
gctcgaccgc tgccaggtcc gcgccggtgg gtcgcagcgg caccaccagg tgctcggaca 300
ggctcatcgc ctgggtgagc aggttcgggt tcttcggccc gacgtcgatc accacgtggg 360
cgtagtcgat cagcatcgga cggagctgcc gggccaggtg ccggtcggcg gcttcgatga 420
cgatgcagcg atccgccggc caatccgcgg cctcctgcga ccaggccaac gccccgtcct 480

```
ggtcggggtc ggcgtcgacg agcagcgtcc ggccctgacg ggcgaggccg agcgccaggt    540
gcaccgccgt cgtggtcttg cccgttccgc ctttgaggtg ccccaccgtg agtctcatga    600
tcactccgcc gctgtcgtcg tatcgtcgac actaccgtca cgacggtgtg ccgctgctgc    660
accccgccgc atgtccccgg tcgtcgtccg ccgcgtggcc gcggtgagcc ggttccaccg    720
cttctgcatc gcctgccgcc cgccgagctg gccgtcgacg gcctcggcga cctgctgcca    780
ggtcatcccc tcgccgcccc atttcagggc tcgcaacaga tcccgctcgt agaaatcggc    840
agcggcacgc atttcctcgc acatacggaa caaagcggct gcctcgccat tggtaaactc    900
gtaatcttcg tcgttgttta ctcgtttatg aaaaacatcc agatagtccg cgctgtgctt    960
tgcaaccgtg tcggaatgct cgatctcctc tgccgggaat tccctcccca gcacttccag   1020
ggcttccctg atctccatac gtcaatcata cgacgacagc gccgtcgtgt caaccttacg   1080
acgatataga cggcaaaccg tttgtacggt tagacggcaa accgtactgg tcgttcgggt   1140
cgactagttg gaatgcggag cctccccgta tcgttactta ggtaccaggc aacaacaggt   1200
agctcggttc ggccgagcag gaggcaagag gaatggcagc gaacaagatc cagcgagtag   1260
acccccgta cgtgcagatc gtcaacgcga tcactgagcg catcgcctcc ggggatctgg   1320
cggtcggtga tcgtgtgccg actgaggctg agatccggga gacctggggc gtctcacgtg   1380
ccacggccaa caaggtcgcg gccgaactga aggcgtccgg cctggcctac acccgccccg   1440
ggtacggact catcgtccga gggcagtccc gcaacgtcgc ctccggtcct gcggccatgt   1500
ggcagcgcat cgcctcgacc ggctcgatct atctgcccaa tgagcactcc gagaggaaga   1560
cgggtgaggc gccggccacc gacgccccgg atgtcgtggt cgcagctctg gatgccaccg   1620
ttttctctca gctcgtttat cggcaccgcg tcatctaccg cgacgcgcac ccgttcacta   1680
ttgctgtctc ctggtttctg cccgcactgc tggaccagca aaagccgatc acggaacgac   1740
tcctgcggaa cgagcgtatt ccggaaggca ccccccgcta catcgccgat cagctcggtc   1800
gagacctcac agagacgacc gagatcgttg gggtagttcg cgcaacggcc gaggaggcag   1860
tggcgctcaa catcaacgag ggggacccgc tcctgcgcgt catctcgacg atcttcgccg   1920
agggctggcc gatcgaggtc ggtgtctacc tctaccccga agcgcccgag atcctgacga   1980
gtcgccacga cctctgaatc tccccagcta gaacgaggta tctaggtagc ttgtccctgt   2040
ggtactgttg aggtacctag gggagcaggg cctaggtacc tcacacggtc cggccccggt   2100
ggcggatcga aacacgggag acgccatgtc gaaccagggt ccgaacagct tcaagatcga   2160
ccaggccgcg accttccaga tggtcatggt catggacgtc gcgccgaagc tgcgtttcgg   2220
cagcgagacc gaccaggagt gcatgaagga cggcaccccg aagtggacgg cgcaggtcac   2280
ggccgggttc cggaccttcg gcgccccgaa gttcgccgtc ctggcgatca ccatcgcctc   2340
gcacgaggac ccccgccagg gtgtccagcc gggcatgccg gtcgagctgg tcggcctgga   2400
ggtcggcgtg atggacaaga agatcaagga ccgcgacacc ggccaggaga aggtcgtcgg   2460
ggcgcaggtc tactaccgcg ccgagggcat ccgcccgatc ggcgccgcga gccacaagcg   2520
cggcgagcag gccgcgtgat gtccggcccg gccgtcctgg tgctggtctg cacctcctgc   2580
cagcacgtca ccgagatcgt cgacgacggc gatcggctgc ctgatcagtg cccgcggtgc   2640
gacggctggg ccttcaccgg aggcctcgtc gccaccacct cgaccgactc gactccgctc   2700
gcccgcgcga gctgaccatg accacggccc cggtccggag accacctccg gtccggggcc   2760
gttctcacga agggggcccc gcgatgggca tctggaccac cgcccgccgg gcggagcgag   2820
```

-continued

```
agcaggaccg ggccgggcgc gagctggtgg accagctcac tgacacgtgg cgccgggcct   2880
gcgagcacgt cgggctgtcc cacgcggtgc aggtcgcctc cggcaccacg atcgtcgtgc   2940
cgacgttggc ccgggccgac gtctccggtc ccgacccggt gctgatcgtc aagttgatgc   3000
cgggccagct ccccgcggac ttccgggccc cggaggtcgc gcagcggctc tcggccgcgc   3060
tgggctgcga ccgcatccgg gtcgagcccc gcggcccgca ctgggtccgg atcgagctgc   3120
tgaccggcga ccccctcgcc gtcgacgtca ccaccgcgct cccggcccgc gaccactcgg   3180
tcagcggagc tcaggtcctc gtcgcccgcg acgagctcgg ccgcccgctg gcgatgcagt   3240
gggaccaggc tccgcacacc tgcgtgcagg gcgcgacccg ctccggtaag tcggtgtggt   3300
gctactcggt gctcgcgcag ctcgcccgcc tcgacgacgt cctgatcgcc ggatccgacc   3360
cgtccgggct gctgctcggt cgcccttggg caggcacccg ccaccacgag tggcaggcca   3420
ccggcagccg cgacgtcctg gcccaccgcg acctgctcga ccgcctggtc gcggagatgg   3480
acgcgcgcat cgccgagctg cccgcacggc aggacaagct cgccgtcttc acccccgccc   3540
ggccgctgat cgtggtcgtc ctcgaggagt tggccggcct tttgcgcctg gcctcgacca   3600
ccccgacccc gaagggcgag gccaaggtcc gcgagcagct cctgcacgcg ttcggccgcc   3660
tggtctcgga gggacacaag gccgggatgc ggctgctggt ggtcacccag cgcgcggacg   3720
tgacgattat cgagggcttc gcccgcggtc agctcgggct gcggctgagc ttccgcgtcg   3780
atgaccccga ggctctggtc atgctccacg gccaggacgc ccgcgccgag ctggtccagc   3840
accgccagtc cccgcccggt gtcgccctgg tccaggcccc cggcatcgcc ctcacccggg   3900
cccgcggccc gcgcctgccc ggcccgtcgg aggacgccga ctacgcacgg ttctgggacg   3960
aggtggcagg ggacgtcccg gcgcgcctcc accaggtagc ggcctgagca ggccagagtc   4020
agcgaccagg ccgacaaaga agtgagcccc caggtgttgg cgcacccagg ggctcgcccg   4080
tcggccggaa gtcatcacca tctgagaacg gatcggaccg gccaacgtgg ctgacctcag   4140
ggtacccacg tgccagcgac tcggctctac gccacgcggg cacatctcca ccccccacac   4200
ctcccgccgc cccgcacggc acgccgtcat gacggtcaac cgtcggcgtc gtcctatcga   4260
cgacagcacc ggatgccgga cggggaacag gagcaccgcc cgtctcgacc gctgcccttc   4320
ctcgatacaa ggccgcacga gtgcggggca ggttcagtca agggtcggcg cagccgatcg   4380
cgtagcgacg ccgcaggcgc ccttggcggg ttctgacctg cattcgacac ttagccgcca   4440
tcgaggtagg gcccaccgca gcacgcgcta cagcaccggc accgagaaca ccctcagctc   4500
tcgcgccgca ggcgcgcgcc cggtccggac gggcccggcc cgcgggccgg aggcaggagc   4560
gggccggagc ccggcccggc cgggcgccgg ccacagcggc ccgatcgctg gcggtgctcg   4620
atgaccgccg cgctgacgcg cgtcgacgcg ggcgtgcccg cgcttggtac tgacgcgaaa   4680
agtgcggcca ccgcaggtca ggtccccgtg ggggactggg cagggagctt ctgggagcgg   4740
caggaccgcg ccttgcggga gaagtaccgg gcccgccgtg agctggccag gatcacgacg   4800
ctgcgtcgcg ttgcacgctg cggacgctcc tcgatgaacg acggcggaga cgtcgtcctg   4860
cgctactcgc ccggcaccgg ggaggacggc tcggcgtcgg cgggtttcgg cggactggtg   4920
acctgcggca gcctgtgggc ctgcccggtc tgctcggcca agatcagcgc ccgccgggcc   4980
cgggagctgg aacacctgat cacctggaac gccgcccgcg gcggcaccgt cgcgctgctc   5040
agcctgacca tgcgccacca cagcggccac cgcctgcgcg acctgcgccg agggctgagc   5100
gccgcgtggc gccacgtcac cagctcccgc gggtggaagc gctggaagag cgtcttggga   5160
atggactacg tccgcgggat tgaggccacc cacggagcga acggctggca tctgcacatc   5220
```

```
cacgccctgc tgatcttccc cggcgacgtc acggaggaga tgcacgccct caccgccgag   5280
atctggaccc gctggtcgac cggcctgcgg cgcaagggct tcgacgccac gatcgcccac   5340
ggcgtcgacg tccgggtcgg caccggcgcc ctcgaacagc tcggccgcta catctccaaa   5400
ctggccttcg agacctccgg cggccggtgg aagctgggca agaacggcag ccgtaccccg   5460
ttccagatcc tcgccgacgc cctggaccga gcccgcgacc gagacctcgc gctctgggcg   5520
gagtgggagc aggccagcca cggcatgcag cagctcgtgt ggtccaacgg actcaaggcg   5580
gcctgccagc tcgacgagat cgacgacgag acgatcgcgg aggaggacga cggtggtgag   5640
ttcgtcgccc agctcccccg ccgcacctgg gagaaggtct accccgtcgc cgaagacctg   5700
atcatcgcca cccgcactgg tggccccgaa gcaggccgcg cctggcttga cgcccgcggc   5760
ctggcctatg accacgagcg cgacacgagc gaacgagcag tcctgctcga cgagccggac   5820
ccgccgttcg cgtggctgag ggccgctctc gcggccgaag accccgagca gcgccgggag   5880
cgacgccgcc gctactaccg caccgcacag accaactgag ctcgatgagg agcagaacca   5940
cgatggccga cacctggacg atcagcccgc tgatccgccc cctgctgcgc aagctcgatg   6000
agcgcggagg ctgcgcctac ccgcaggact tcccgcactg ccacggcgcc gagatccagc   6060
acaccgacgg caccgccgaa tgcttcaacc ccggccagcc ctgcccctac ccacgacccg   6120
gcgcgcacgc cttcgtccac acctgcgctg acgtcaccca ccggctcacc caccgctgca   6180
cccgctgccg ctgattcacc acaggccatg cacctatgca ttgcccaatg atgatcttcg   6240
gctgctgacg tcgtcgatac gacgacatta ctcaattctg ttgtcccata aagcatctgg   6300
cctctaatgg ccccaaccag tcgactgact ggcccacact tacatatatg tagtttcgcg   6360
ctgtaaaggg tattcatccc atttggcggc taccggtcac actatcgatt ttggaagggt   6420
ctgtgacccg aagtaattcg acctcaagcc actggggcct taaatgaaga ctctcgctcg   6480
tccggtcaaa tccgcggcag tatcactctt ggcggctgtc gctctgttcg gtactgcggc   6540
agcaagtcct atcgcgcccc aggcttcggc gaacccagtt ggaaactgtg gggctctgt    6600
ccagacctat cgccagaacg gcccaattga cgcctggcgg gtgcgggtca ccggagtgga   6660
tctgatgggg atcatcaggc ctgcggtgcg aggcgagttc aacatgtcga tcagtggacc   6720
ggacggcgaa tcatttctcg ctcgttcgat tccgttcgat gaatttactg gaccgagtga   6780
tagcgttatc gtcagaggac cggaggtccg ggtctcggtc caggtcgttg ctacgcctgc   6840
caacggcagg agctgcagct actactacgt ggcaccctat ccgggtgcgt aagtaacagc   6900
gagagtggga aatgactcat ccagcgttgg gccgactcaa gagactgaac gcagcggtca   6960
atgaagtagg gctgtctgag tccgaggaag agccgctgac tgctgaggcc ctcaaagagg   7020
cgatctcgca tttctcaaca ttgttgttcc agctcggaat aagtgctggc tacttcaacg   7080
actccgatct agcgaagacg ctagaccttg atgacaagtg gagagacttt ttcaccgatc   7140
tgagcgcggc gcagcgttct gccttttatc tactggaggc gagcgtaggt gagagggctc   7200
cacaggaacc ggatgacggc tctaggccct ggatcggtcc gcactaatcg aggcttgact   7260
aagggggtat ctctgccttg gctggcgtgc ggttgagagc cggtccgccc tgaacactga   7320
gtggtgtcgt cgataggacg acggggccgg atatgactac agtcggtgac cacgcgtccc   7380
tcaagatcgt ttgatgcata ggtgtgagtc aattgatctt ggtcgggggt gtgactggct   7440
gtggtcagac ggggctgacg ccggtctcgg cgttggcgtg ctggcacaga acgaggacgc   7500
gatcgccgtc ggtgccgcgg tagatcgtct ggccgtcgta gtcggtcagg tggtggatcg   7560
```

gcgcgggctc gccggagatc ttccggacgg cgtgggtcca gggcggcggg tgccggtcgg 7620
tgatcttctc ggtcatcgcc gcggcgcctg cttgccgatc atcgtgacga cctggtcgcg 7680
caggctcgcg tcgtcggcgg cgagcagcac gagagcggac aggacctcga tccggtccac 7740
gtggcggccc agccgtcgcc gcgctacccg ggccaggtgc tcgaacgcgt cgcgggtgtc 7800
gtcgtcgagg accgcggtgt acttcgaccc gccccgcgcc ggacgtaccg cggggacctc 7860
acgcggctgc ggtggtgcgg ccaccggctc ggcgaccgcg accggcaccg gcgtcccggg 7920
cagggtgatc tggtccgggt gctgcgggtg ctcgacgggc gtgtcgtcgt tacgacgacc 7980
tttggtggag gcggcggccg cgaggctgcg acgggctccg gctcgcttgc gctcagccat 8040
gatcagg 8047

<210> SEQ ID NO 13
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 13
atcaccgggg agaacttcac cgaggtcgcc 30

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 14
cggggtgggg ttctcgaagt actggccctt 30

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
gggtgccctc gacgagctcg a 21

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
acgcgatggg caccgcgctg t 21

<210> SEQ ID NO 17
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 17
gccggatccc tcccgccgcc ccgcacggca 30

<210> SEQ ID NO 18
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 18
gcctgtacat gacccgcacc cgccaggcgt 30

<210> SEQ ID NO 19
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 19
gcctgtacac tcccgccgcc ccgcacggca 30

<210> SEQ ID NO 20
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 20
gccggatcct gacccgcacc cgccaggcgt 30

<210> SEQ ID NO 21
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 21
gccggatccg gttctgacct gcattcgaca 30

<210> SEQ ID NO 22
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 22
gccggatccg atcgctggcg gtgctcgatg 30

<210> SEQ ID NO 23
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 23
gcctgtacac aggcgcggcc tgcttcgggg 30

<210> SEQ ID NO 24
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 24
gcctgtacag cgggctgatc gtccaggtgt 30

<210> SEQ ID NO 25
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 25
gcctgtacaa ttagaggcca gatgctttat 30

<210> SEQ ID NO 26
<211> LENGTH: 448
<212> TYPE: DNA
<213> ORGANISM: Pseudonocardia autotrophica

<400> SEQUENCE: 26
gtgcctggcc tgctcggccg cggcgacgag ggtctcccgc agcagcggca ggacctgcgc 60
cagcggatgt ccggcgcgca gctcggcgac ctcgcccggc tggtaggtgt gcgagggccg 120
ggaccgctcc ggatcgacgg cggcggccag cgaacgctcc caggacgccc ggatctccgg 180
gcgcacctcc ggtgcggccg aaccggtcag cgcggcgcca cgcgcccgct ccagcccgcc 240
tcgttcacgc gtcacgacac tcaccctatg gttagctcag ccttacctga atcgaatccg 300
cgggatcggc actctccgga ggttcaggtt ccgcatctgc gtgcaacccc tgtgcaaccc 360
ccaccttcct agtgtccggc atcacgcgca atgcagtgat atctccacgg acatccccca 420
cggacatccc ccacgggaag gaccatcg 448

<210> SEQ ID NO 27
<211> LENGTH: 3200
<212> TYPE: DNA
<213> ORGANISM: Pseudonocardia autotrophica

<400> SEQUENCE: 27
cactcccgaa acagggatca tgctcgccgg ccgggacgag tggggtggat cagccgtcgg 60
gcagcgccag gtcgcgatgg tccccgtccg gtagcgcccg ccgcagccgg tcccgcagct 120
cggtgtccgg atcgctgtcc ggatcggcgc gcagcagcgc gagcagcgcc tccggatcgc 180
ccgagcgcag tacggcggta cgggtcgagg ccaccaggtg ctcgcgctcg gcccgcacac 240
ccggcgactc cgaggtcggc agcaacggac cgcgggccgc ctcggccgcg gcgtcgcgga 300
cccgcccgtg ccgcagcgcc tcgcgcagcc ggaggaagtc ggcgtccacc cgggcggcga 360
gccgataggg ctgggtacgg acggtgtcct cgccgacgca gcggcgcagc cggtgcatct 420
cggcccggac ggtgatcggg cgcccctcgt cgccgtagag cgcgccggcg agctggtcgg 480
ccgtcagccc ctctgggtgc agcgcgagca gggtgagcac ctcggcgtgc cgcagcccga 540
gccgcagcgg ccggccgtcg cgccgggcga ccggcgccct ggccccgagg aacggcaggg 600
tgagcgccgg cagcaccgga cccgagggtg tgggcacccg gagcagccag ccctcgccca 660
gcggctccag cacggcctcg gcgccgccgt cgagcaggat ccggtcgccg cgctcgggca 720
gcgtcacccg gacagggaag cggtgcgccg gggtggcggc cagcacccgg ccgtgtggtg 780
acagcagcgc gccggggacg tcgccgagcc gggacaggtg cggcaggttg gtgtcccgca 840
atcgccggtc acgatcctcc agcagcgccg ccagccggtg ctcggcgagc cgcgcggccg 900
cggtgaccag cgacagcgtc atcggatgga acgactcctc cggcccggtg acgtcgacgg 960

```
cgccgatctg gcggccggtc tccgggtcgt gcaccggagc ggccgcgcag gtccacgggt   1020
gataggcgct gaccaggtgc tcggccgagt ggatccggac cggccggtcg tcggacagcg   1080
cggtgcccat cgcgttggtg ccgaccgagt cctcgctcca gcgggtgccc tcgacgagct   1140
cgacccgctc ggcccggcgc agcacctcgc gcgcaccctc ccgccacagg atgtgcccgc   1200
gctcgtcggt cacgatcatc atgtgcctgg cctgctcggc cgcggcgacg agggtctccc   1260
gcagcagcgg caggacctgc gccagcggat gtccggcgcg cagctcggcg acctcgcccg   1320
gctggtaggt gtgcgagggc cgggaccgct ccggatcgac ggcggcggcc agcgaacgct   1380
cccaggacgc ccggatctcc gggcgcacct ccggtgcggc cgaaccggtc agcgcggcgc   1440
cacgcgcccg ctccagcccg cctcgttcac gcgtcacgac actcacccta tggttagctc   1500
agccttacct gaatcgaatc cgcgggatcg gcactctccg gaggttcagg ttccgcatct   1560
gcgtgcaacc cctgtgcaac ccccaccttc ctagtgtccg gcatcacgcg caatgcagtg   1620
atatctccac ggacatcccc cacggacatc ccccacggga aggaccatcg atggccacgt   1680
acgcggcacc gggtcagccg gacagcgtcg tctcgttcaa gcctcgctac gaccacttca   1740
tcggcggcga gtacatcgcg ccggcgaagg gccagtactt cgagaacccc accccgatca   1800
ccggggagaa cttcaccgag gtcgcccgcg gcaccgccga cgacgtcgag aaggccctcg   1860
acgcggcgca cggcgccgca ccggcctggg gcaagacctc gcccaccgag cgggcgaaca   1920
tcctgaacaa gatggccgac cggatcgagg cgaacctcga ggcggtcgcg atcgccgagt   1980
cctgggagaa cggcaaggcc tgccgggaga ccctggcggc cgacatcccg ctggcgatcg   2040
accacctgcg ctacttcgcc ggtgcgatcc gggcgcagga gggcggtctc tcccagatcg   2100
acgacgacac cgtcgcctac cacttccacg agccgctggg cgtcgtcggc cagatcatcc   2160
cgtggaactt cccgatcctg atggcgatct ggaagctcgc cccggcgctc gccgcaggca   2220
acgcgatcgt cctcaagccg gccgagcaga cgccggtctc gatccacgtc ctgctggacc   2280
tggtcgccga cctgctgccg cccggtgtgc tcaacatcgt caacgggttc ggcgtcgagg   2340
ccggcaagcc gctggcgtcc aacaagcgca tctcgaagat cgccttcacc ggtgagacca   2400
ccaccggccg gctgatcatg cagtacgcct cggagaacct gatcccggtc accctggagc   2460
tgggtggcaa gagcccgaac atcttcttcg acgacgtcgc ctcccagcag gacgcgttct   2520
acgacaaggc gctcgagggc ttcgcgatgt tcgccctcaa ccagggcgag gtctgcacct   2580
gcccgtcgcg cgcgctgatc cagggcggca tctaccagga gttcctggag caggcggtca   2640
agcgcaccga gcagatcaag cagggcaacc cgctcgacac cgacacccag atcggtgcgc   2700
aggcctcgaa cgaccagttc gagaagatcc tgtcctacat cgacatcggt cgtcaggagg   2760
gggccaaggt cctcaccggt ggcgagaagg ccgatctcgg cggcgacctc tccggcggct   2820
actacatcaa gccgaccgtg ttcgagggca acaaccagat gcggatcttc caggaggaga   2880
tcttcggtcc ggtcgtctcg gtggcccggt tctccgacta cgacgacgcc atccggaccg   2940
ccaacgacac gctctacggc ctcggcgccg gcgtgtggag ccgggacacg aacaccgcct   3000
accgggcggg tcgcgacatc caggccggcc gggtgtgggt gaacaactac cacgcgtacc   3060
cggcgcacgc tgccttcggc ggctacaagc agtccggcat cgggcgcgag aaccacaagc   3120
agatgctcga ccactaccag cagaccaaga acgtcctgca gagctactcg ccgaacgcgc   3180
tgggcttctt ctgatggggc                                                 3200
```

<210> SEQ ID NO 28

<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 28
gcctgtacat cgcggacgtg ctcatagtcc 30

<210> SEQ ID NO 29
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 29
gccggatccc ctgatagaaa cagaagccac 30

<210> SEQ ID NO 30
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 30
gtcccggcaa cgctgggtgg atggatccat 30

<210> SEQ ID NO 31
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 31
gccggtaccc caaaatccct taacgtgagt 30

<210> SEQ ID NO 32
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 32
gccggtaccc tcccgccgcc ccgcacggca 30

<210> SEQ ID NO 33
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 33
gccaagcttg tgcctggcct gctcggccgc 30

<210> SEQ ID NO 34
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 34
gcccatatgt ggtccttccc gtgggggatg 30

<210> SEQ ID NO 35
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 35
gccccccata tggcgctgac caccaccggc 30

<210> SEQ ID NO 36
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 36
gccgctagct caggcgctgc gcggccccat 30

<210> SEQ ID NO 37
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 37
gcccaattga ctagtcgacc caccggcacc 30

<210> SEQ ID NO 38
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 38
gcccttaagt agagtcccgc tgaggcggcg 30

<210> SEQ ID NO 39
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 39
gcccatatga ccgagaccgt tacgacgccc 30

<210> SEQ ID NO 40
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 40
gccactagtc tactcgacga cgcgtaccgc 30

<210> SEQ ID NO 41
<211> LENGTH: 30
<212> TYPE: DNA

<213> ORGANISM: Artificial Sequence
<220> FEATURE:
<223> OTHER INFORMATION: Synthetic oligonucleotide

<400> SEQUENCE: 41
gccggtaccg tgcctggcct gctcggccgc 30

<210> SEQ ID NO 42
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 42
gccggtacct agagtcccgc tgaggcggcg 30

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 43
ctacactaga aggacagtat t 21

<210> SEQ ID NO 44
<211> LENGTH: 1212
<212> TYPE: DNA
<213> ORGANISM: Pseudonocardia autotrophica

<400> SEQUENCE: 44
atggcgctga ccaccaccgg caccgagcag cacgacctgt tctcgggcac cttctggcag 60
aacccgcatc ccgcctacgc ggcactccgt gccgaggatc cggtacgcaa gctcgcgctg 120
ccggacgggc cggtctggct gctcacccgc tacgccgacg tgcgcgaggc gttcgtcgat 180
ccgcgcctgt cgaaggactg gcgccacacg ctgcccgagg accagcgggc ggacatgccg 240
gccacgccga cgccgatgat gatcctgatg gatccgccgg atcacacccg gctgcgcaag 300
ctggtcggca ggtcgttcac cgtccgccgg atgaacgagc tggagccgcg gatcaccgag 360
atcgccgacg gcctgctcgc cggcctgccc accgacggcc cggtcgacct gatgcgcgag 420
tacgcgttcc agatcccggt acaggtgatc tgcgagctgc tcggggtgcc cgccgaggac 480
cgcgacgact tctccgcgtg gtcgtcggtg ctggtcgacg actcgccggc cgacgacaag 540
aacgcggcca tgggcaagct gcacggctac ctgtccgacc tgctggagcg caagcgcacc 600
gagcccgacg acgcgctgtt gtcgtcgctg ctggcggtgt ccgacgagga cggcgaccgg 660
ctctcccagg aggagctcgt cgcgatggcg atgctgctgc tgatcgccgg gcacgagacg 720
acggtcaacc tgatcggcaa cggcgtcctc gccctgctca cgcaccccga ccagcggaag 780
ctgctggccg aggacccgtc gctgatcagc tcggcggtcg aggagttcct gcggttcgac 840
tctcccgtct cgcaggcccc gatccggttc accgcggagg acgtcaccta ctccggcgtg 900
accatcccgg ccggcgagat ggtcatgctc gggctggccg ccgccaaccg ggacgccgac 960
tggatgcccg agccggaccg gctcgacatc acccgggacg cctccggcgg ggtgttcttc 1020
gggcacggca tccacttctg cctcggtgcc cagctggccc ggctggaggg ccgggtcgcg 1080
atcggacggc tgttcgccga tcgcccggag ctggcgctcg cggtcggcct cgacgagctg 1140
gtctaccggg agtcgacgct ggtccggggg ctgtcgagga tgccggtgac gatggggccg 1200
cgcagcgcct ga 1212

<210> SEQ ID NO 45
<211> LENGTH: 7510
<212> TYPE: DNA
<213> ORGANISM: Artificial Sequence
<220> FEATURE:
<223> OTHER INFORMATION: Synthetic polynucleotide

<400> SEQUENCE: 45
tgtacatcgc ggacgtgctc atagtccacg acgcccgtga ttttgtagcc ctggccgacg 60
gccagcaggt aggccgacag gctcatgccg gccgccgccg ccttttcctc aatcgctctt 120
cgttcgtctg gaaggcagta caccttgata ggtgggctgc ccttcctggt tggcttggtt 180
tcatcagcca tccgcttgcc ctcatctgtt acgccggcgg tagccggcca gcctcgcaga 240
gcaggattcc cgttgagcac cgccaggtgc gaataaggga cagtgaagaa ggaacacccg 300
ctcgcgggtg ggcctacttc acctatcctg ccccgctgac gccgttggat acaccaagga 360
aagtctacac gaaccctttg gcaaaatcct gtatatcgtg cgaaaaagga tggatatacc 420
gaaaaaatcg ctataatgac cccgaagcag ggttatgcag cggaaaagcg ctgcttccct 480
gctgttttgt ggaatatcta ccgactggaa acaggcaaat gcaggaaatt actgaactga 540
ggggacaggc gagagacgat gccaaagagc tcctgaaaat ctcgataact caaaaaatac 600
gcccggtagt gatcttattt cattatggtg aaagttggaa cctcttacgt gccgatcaac 660
gtctcatttt cgccaaaagt tggcccaggg cttcccggta tcaacaggga caccaggatt 720
tatttattct gcgaagtgat cttccgtcac aggtatttat tcggcgcaaa gtgcgtcggg 780
tgatgctgcc aacttactga tttagtgtat gatggtgttt ttgaggtgct ccagtggctt 840
ctgtttctat cagctcctga aaatctcgat aactcaaaaa atacgcccgg tagtgatctt 900
atttcattat ggtgaaagtt ggaacctctt acgtgccgat caacgtctca ttttcgccaa 960
aagttggccc agggcttccc ggtatcaaca gggacaccag gatttattta ttctgcgaag 1020
tgatcttccg tcacaggtat ttattcggcg caaagtgcgt cgggtgatgc tgccaactta 1080
ctgatttagt gtatgatggt gtttttgagg tgctccagtg gcttctgttt ctatcagggg 1140
atccatgccg tatttgcagt accagcgtac ggcccacaga atgatgtcac gctgaaaatg 1200
ccggcctttg aatgggttca tgtgcagctc catcagcaaa aggggatgat aagtttatca 1260
ccaccgacta tttgcaacag tgccgttgat cgtgctatga tcgactgatg tcatcagcgg 1320
tggagtgcaa tgtcgtgcaa tacgaatggc gaaaagccga gctcatcggt cagcttctca 1380
accttggggt taccccccggc ggtgtgctgc tggtccacag ctccttccgt agcgtccggc 1440
ccctcgaaga tgggccactt ggactgatcg aggccctgcg tgctgcgctg ggtccgggag 1500
ggacgctcgt catgccctcg tggtcaggtc tggacgacga gccgttcgat cctgccacgt 1560
cgcccgttac accggacctt ggagttgtct ctgacacatt ctggcgcctg ccaaatgtaa 1620
agcgcagcgc ccatccattt gcctttgcgg cagcggggcc acaggcagag cagatcatct 1680
ctgatccatt gcccctgcca cctcactcgc ctgcaagccc ggtcgcccgt gtccatgaac 1740
tcgatgggca ggtacttctc ctcggcgtgg gacacgatgc caacacgacg ctgcatcttg 1800
ccgagttgat ggcaaaggtt ccctatgggg tgccgagaca ctgcaccatt cttcaggatg 1860
gcaagttggt acgcgtcgat tatctcgaga atgaccactg ctgtgagcgc tttgccttgg 1920
cggacaggtg gctcaaggag aagagccttc agaaggaagg tccagtcggt catgcctttg 1980

-continued

```
ctcggttgat ccgctcccgc gacattgtgg cgacagccct gggtcaactg ggccgagatc   2040
cgttgatctt cctgcatccg ccagaggcgg gatgcgaaga atgcgatgcc gctcgccagt   2100
cgattggctg agctcatgag cggagaacga gatgacgttg gaggggcaag gtcgcgctga   2160
ttgctggggc aacacgtgga gcggatcggg gattgtcttt cttcagctcg ctgatgatat   2220
gctgacgctc aatgccgttt ggcctccgac taacgaaaat cccgcatttg gacggctgat   2280
ccgattggca cggcggacgg cgaatggcgg agcagacgct cgtccggggg caatgagata   2340
tgaaaaagcc tgaactcacc gcgacgtaag cttgtgcctg gcctgctcgg ccgcggcgac   2400
gagggtctcc cgcagcagcg gcaggacctg cgccagcgga tgtccggcgc gcagctcggc   2460
gacctcgccc ggctggtagg tgtgcgaggg ccgggaccgc tccggatcga cggcggcggc   2520
cagcgaacgc tcccaggacg cccggatctc cgggcgcacc tccggtgcgg ccgaaccggt   2580
cagcgcggcg ccacgcgccc gctccagccc gcctcgttca cgcgtcacga cactcaccct   2640
atggttagct cagccttacc tgaatcgaat ccgcgggatc ggcactctcc ggaggttcag   2700
gttccgcatc tgcgtgcaac ccctgtgcaa cccccacctt cctagtgtcc ggcatcacgc   2760
gcaatgcagt gatatctcca cggacatccc ccacggacat cccccacggg aaggaccatc   2820
gcatatggcg ctgaccacca ccggcaccga gcagcacgac ctgttctcgg gcaccttctg   2880
gcagaacccg catcccgcct acgcggcact ccgtgccgag gatccggtac gcaagctcgc   2940
gctgccggac gggccggtct ggctgctcac ccgctacgcc gacgtgcgcg aggcgttcgt   3000
cgatccgcgc ctgtcgaagg actggcgcca cacgctgccc gaggaccagc gggcggacat   3060
gccggccacg ccgacgccga tgatgatcct gatggatccg ccggatcaca cccggctgcg   3120
caagctggtc ggcaggtcgt tcaccgtccg ccggatgaac gagctggagc cgcggatcac   3180
cgagatcgcc gacggcctgc tcgccggcct gcccaccgac ggcccggtcg acctgatgcg   3240
cgagtacgcg ttccagatcc cggtacaggt gatctgcgag ctgctcgggg tgcccgccga   3300
ggaccgcgac gacttctccg cgtggtcgtc ggtgctggtc gacgactcgc cggccgacga   3360
caagaacgcg gccatgggca agctgcacgg ctacctgtcc gacctgctgg agcgcaagcg   3420
caccgagccc gacgacgcgc tgttgtcgtc gctgctggcg gtgtccgacg aggacggcga   3480
ccggctctcc caggaggagc tcgtcgcgat ggcgatgctg ctgctgatcg ccgggcacga   3540
gacgacggtc aacctgatcg gcaacggcgt cctcgccctg ctcacgcacc ccgaccagcg   3600
gaagctgctg gccgaggacc cgtcgctgat cagctcggcg gtcgaggagt tcctgcggtt   3660
cgactctccc gtctcgcagg ccccgatccg gttcaccgcg gaggacgtca cctactccgg   3720
cgtgaccatc ccggccggcg agatggtcat gctcgggctg gccgccgcca accgggacgc   3780
cgactggatg cccgagccgg accggctcga catcacccgg gacgcctccg gcggggtgtt   3840
cttcgggcac ggcatccact tctgcctcgg tgcccagctg gcccggctgg agggccgggt   3900
cgcgatcgga cggctgttcg ccgatcgccc ggagctggcg ctcgcggtcg gcctcgacga   3960
gctggtctac cgggagtcga cgctggtccg ggggctgtcg aggatgccgg tgacgatggg   4020
gccgcgcagc gcctgagcta gcgttaacgc ggccgcgaat tcaggcctat gcattacgta   4080
caattgacta gtcgacccac cggcacccgt gagcccctcg ctgcgggtgc cggtgcgagg   4140
gactgcaaca cgcgaaacct gcacaaacac acggaggttg gaatgagcgc cacggacaca   4200
cccgataccg gcgccgttcc accccggttg gtgaccaccg ctggggcggc tgacctgcta   4260
cgccgcctca gcgggactct acttaagcag cttgagtatt ctatagtgtc acctaaatag   4320
cttggcgtaa tcatggtcat agctgtttcc tgtgtgaaat tgttatccgc tcacaattcc   4380
```

```
acacaacata cgagccggaa gcataaagtg taaagcctgg ggtgcctaat gagtgagcta   4440
actcacatta attgcgttgc gctcactgcc cgctttccag tcgggaaacc tgtcgtgcca   4500
gctgcattaa tgaatcggcc aacgcgcggg gagaggcggt ttgcgtattg ggcgctcttc   4560
cgcttcctcg ctcactgact cgctgcgctc ggtcgttcgg ctgcggcgag cggtatcagc   4620
tcactcaaag gcggtaatac ggttatccac agaatcaggg gataacgcag gaaagaacat   4680
gtgagcaaaa ggccagcaaa aggccaggaa ccgtaaaaag gccgcgttgc tggcgttttt   4740
cgataggctc cgcccccctg acgagcatca caaaaatcga cgctcaagtc agaggtggcg   4800
aaacccgaca ggactataaa gataccaggc gtttccccct ggaagctccc tcgtgcgctc   4860
tcctgttccg accctgccgc ttaccggata cctgtccgcc tttctccctt cgggaagcgt   4920
ggcgctttct catagctcac gctgtaggta tctcagttcg gtgtaggtcg ttcgctccaa   4980
gctgggctgt gtgcacgaac cccccgttca gcccgaccgc tgcgccttat ccggtaacta   5040
tcgtcttgag tccaacccgg taagacacga cttatcgcca ctggcagcag ccactggtaa   5100
caggattagc agagcgaggt atgtaggcgg tgctacagag ttcttgaagt ggtggcctaa   5160
ctacggctac actagaagga cagtatttgg tatctgcgct ctgctgaagc cagttacctt   5220
cggaaaaaga gttggtagct cttgatccgg caaacaaacc accgctggta gcggtggttt   5280
ttttgtttgc aagcagcaga ttacgcgcag aaaaaaagga tctcaagaag atcctttgat   5340
cttttctacg gggtctgacg ctcagtggaa cgaaaactca cgttaaggga ttttggggta   5400
ccctcccgcc gccccgcacg gcacgccgtc atgacggtca accgtcggcg tcgtcctatc   5460
gacgacagca ccggatgccg gacggggaac aggagcaccg cccgtctcga ccgctgccct   5520
tcctcgatac aaggccgcac gagtgcgggg caggttcagt caagggtcgg cgcagccgat   5580
cgcgtagcga cgccgcaggc gcccttggcg ggttctgacc tgcattcgac acttagccgc   5640
catcgaggta gggcccaccg cagcacgcgc tacagcaccg gcaccgagaa caccctcagc   5700
tctcgcgccg caggcgcgcg cccggtccgg acgggcccgg cccgcgggcc ggaggcagga   5760
gcgggccgga gcccggcccg gccgggcgcc ggccacagcg gcccgatcgc tggcggtgct   5820
cgatgaccgc cgcgctgacg cgcgtcgacg cgggcgtgcc cgcgcttggt actgacgcga   5880
aaagtgcggc caccgcaggt caggtccccg tgggggactg ggcagggagc ttctgggagc   5940
ggcaggaccg cgccttgcgg gagaagtacc gggcccgccg tgagctggcc aggatcacga   6000
cgctgcgtcg cgttgcacgc tgcggacgct cctcgatgaa cgacggcgga gacgtcgtcc   6060
tgcgctactc gcccggcacc ggggaggacg gctcggcgtc ggcgggtttc ggcggactgg   6120
tgacctgcgg cagcctgtgg gcctgcccgg tctgctcggc caagatcagc gcccgccggg   6180
cccgggagct ggaacacctg atcacctgga acgccgcccg cggcggcacc gtcgcgctgc   6240
tcagcctgac catgcgccac cacagcggcc accgcctgcg cgacctgcgc cgagggctga   6300
gcgccgcgtg gcgccacgtc accagctccc gcgggtggaa gcgctggaag agcgtcttgg   6360
gaatggacta cgtccgcggg attgaggcca cccacggagc gaacggctgg catctgcaca   6420
tccacgccct gctgatcttc cccggcgacg tcacggagga gatgcacgcc ctcaccgccg   6480
agatctggac ccgctggtcg accggcctgc ggcgcaaggg cttcgacgcc acgatcgccc   6540
acggcgtcga cgtccgggtc ggcaccggcg ccctcgaaca gctcggccgc tacatctcca   6600
aactggcctt cgagacctcc ggcggccggt ggaagctggg caagaacggc agccgtaccc   6660
cgttccagat cctcgccgac gccctggacc gagcccgcga ccgagacctc gcgctctggg   6720
```

```
cggagtggga gcaggccagc cacggcatgc agcagctcgt gtggtccaac ggactcaagg   6780

cggcctgcca gctcgacgag atcgacgacg agacgatcgc ggaggaggac gacggtggtg   6840

agttcgtcgc ccagctcccc cgccgcacct gggagaaggt ctaccccgtc gccgaagacc   6900

tgatcatcgc cacccgcact ggtggccccg aagcaggccg cgcctggctt gacgcccgcg   6960

gcctggccta tgaccacgag cgcgacacga gcgaacgagc agtcctgctc gacgagccgg   7020

acccgccgtt cgcgtggctg agggccgctc tcgcggccga agaccccgag cagcgccggg   7080

agcgacgccg ccgctactac cgcaccgcac agaccaactg agctcgatga ggagcagaac   7140

cacgatggcc gacacctgga cgatcagccc gctgatccgc cccctgctgc gcaagctcga   7200

tgagcgcgga ggctgcgcct acccgcagga cttcccgcac tgccacggcg ccgagatcca   7260

gcacaccgac ggcaccgccg aatgcttcaa ccccggccag ccctgcccct acccacgacc   7320

cggcgcgcac gccttcgtcc acacctgcgc tgacgtcacc caccggctca cccaccgctg   7380

cacccgctgc cgctgattca ccacaggcca tgcacctatg cattgcccaa tgatgatctt   7440

cggctgctga cgtcgtcgat acgacgacat tactcaattc tgttgtccca taaagcatct   7500

ggcctctaat                                                          7510
```

<210> SEQ ID NO 46
<211> LENGTH: 7685
<212> TYPE: DNA
<213> ORGANISM: Artificial Sequence
<220> FEATURE:
<223> OTHER INFORMATION: Synthetic polynucleotide

<400> SEQUENCE: 46

```
tgtacatcgc ggacgtgctc atagtccacg acgcccgtga ttttgtagcc ctggccgacg     60

gccagcaggt aggccgacag gctcatgccg gccgccgccg ccttttcctc aatcgctctt    120

cgttcgtctg gaaggcagta caccttgata ggtgggctgc ccttcctggt tggcttggtt    180

tcatcagcca tccgcttgcc ctcatctgtt acgccggcgg tagccggcca gcctcgcaga    240

gcaggattcc cgttgagcac cgccaggtgc gaataaggga cagtgaagaa ggaacacccg    300

ctcgcgggtg ggcctacttc acctatcctg ccccgctgac gccgttggat acaccaagga    360

aagtctacac gaaccctttg gcaaaatcct gtatatcgtg cgaaaaagga tggatatacc    420

gaaaaaatcg ctataatgac cccgaagcag ggttatgcag cggaaaagcg ctgcttccct    480

gctgttttgt ggaatatcta ccgactggaa acaggcaaat gcaggaaatt actgaactga    540

ggggacaggc gagagacgat gccaaagagc tcctgaaaat ctcgataact caaaaaatac    600

gcccggtagt gatcttattt cattatggtg aaagttggaa cctcttacgt gccgatcaac    660

gtctcatttt cgccaaaagt tggcccaggg cttcccggta tcaacaggga caccaggatt    720

tatttattct gcgaagtgat cttccgtcac aggtatttat tcggcgcaaa gtgcgtcggg    780

tgatgctgcc aacttactga tttagtgtat gatggtgttt ttgaggtgct ccagtggctt    840

ctgtttctat cagctcctga aaatctcgat aactcaaaaa atacgcccgg tagtgatctt    900

atttcattat ggtgaaagtt ggaacctctt acgtgccgat caacgtctca ttttcgccaa    960

aagttggccc agggcttccc ggtatcaaca gggacaccag gatttattta ttctgcgaag   1020

tgatcttccg tcacaggtat ttattcggcg caaagtgcgt cgggtgatgc tgccaactta   1080

ctgatttagt gtatgatggt gtttttgagg tgctccagtg gcttctgttt ctatcagggg   1140

atccatgccg tatttgcagt accagcgtac ggcccacaga atgatgtcac gctgaaaatg   1200

ccggcctttg aatgggttca tgtgcagctc catcagcaaa aggggatgat aagtttatca   1260
```

```
ccaccgacta tttgcaacag tgccgttgat cgtgctatga tcgactgatg tcatcagcgg   1320
tggagtgcaa tgtcgtgcaa tacgaatggc gaaaagccga gctcatcggt cagcttctca   1380
accttggggt tacccccggc ggtgtgctgc tggtccacag ctccttccgt agcgtccggc   1440
ccctcgaaga tgggccactt ggactgatcg aggccctgcg tgctgcgctg ggtccgggag   1500
ggacgctcgt catgccctcg tggtcaggtc tggacgacga gccgttcgat cctgccacgt   1560
cgcccgttac accggacctt ggagttgtct ctgacacatt ctggcgcctg ccaaatgtaa   1620
agcgcagcgc ccatccattt gcctttgcgg cagcggggcc acaggcagag cagatcatct   1680
ctgatccatt gcccctgcca cctcactcgc ctgcaagccc ggtcgcccgt gtccatgaac   1740
tcgatgggca ggtacttctc ctcggcgtgg gacacgatgc caacacgacg ctgcatcttg   1800
ccgagttgat ggcaaaggtt ccctatgggg tgccgagaca ctgcaccatt cttcaggatg   1860
gcaagttggt acgcgtcgat tatctcgaga atgaccactg ctgtgagcgc tttgccttgg   1920
cggacaggtg gctcaaggag aagagccttc agaaggaagg tccagtcggt catgcctttg   1980
ctcggttgat ccgctcccgc gacattgtgg cgacagccct gggtcaactg ggccgagatc   2040
cgttgatctt cctgcatccg ccagaggcgg gatgcgaaga atgcgatgcc gctcgccagt   2100
cgattggctg agctcatgag cggagaacga gatgacgttg gaggggcaag gtcgcgctga   2160
ttgctggggc aacacgtgga gcggatcggg gattgtcttt cttcagctcg ctgatgatat   2220
gctgacgctc aatgccgttt ggcctccgac taacgaaaat cccgcatttg gacggctgat   2280
ccgattggca cggcggacgg cgaatggcgg agcagacgct cgtccggggg caatgagata   2340
tgaaaaagcc tgaactcacc gcgacgtaag ctttaagcag cttgagtatt ctatagtgtc   2400
acctaaatag cttggcgtaa tcatggtcat agctgtttcc tgtgtgaaat tgttatccgc   2460
tcacaattcc acacaacata cgagccggaa gcataaagtg taaagcctgg ggtgcctaat   2520
gagtgagcta actcacatta attgcgttgc gctcactgcc cgctttccag tcgggaaacc   2580
tgtcgtgcca gctgcattaa tgaatcggcc aacgcgcggg gagaggcggt ttgcgtattg   2640
ggcgctcttc cgcttcctcg ctcactgact cgctgcgctc ggtcgttcgg ctgcggcgag   2700
cggtatcagc tcactcaaag gcggtaatac ggttatccac agaatcaggg gataacgcag   2760
gaaagaacat gtgagcaaaa ggccagcaaa aggccaggaa ccgtaaaaag gccgcgttgc   2820
tggcgttttt cgataggctc cgcccccctg acgagcatca caaaaatcga cgctcaagtc   2880
agaggtggcg aaacccgaca ggactataaa gataccaggc gtttccccct ggaagctccc   2940
tcgtgcgctc tcctgttccg accctgccgc ttaccggata cctgtccgcc tttctccctt   3000
cgggaagcgt ggcgctttct catagctcac gctgtaggta tctcagttcg gtgtaggtcg   3060
ttcgctccaa gctgggctgt gtgcacgaac cccccgttca gcccgaccgc tgcgccttat   3120
ccggtaacta tcgtcttgag tccaacccgg taagacacga cttatcgcca ctggcagcag   3180
ccactggtaa caggattagc agagcgaggt atgtaggcgg tgctacagag ttcttgaagt   3240
ggtggcctaa ctacggctac actagaagga cagtatttgg tatctgcgct ctgctgaagc   3300
cagttacctt cggaaaaaga gttggtagct cttgatccgg caaacaaacc accgctggta   3360
gcggtggttt ttttgtttgc aagcagcaga ttacgcgcag aaaaaaagga tctcaagaag   3420
atcctttgat cttttctacg gggtctgacg ctcagtggaa cgaaaactca cgttaaggga   3480
ttttggggta cctagagtcc cgctgaggcg gcgtagcagg tcagccgccc cagcggtggt   3540
caccaaccgg ggtggaacgg cgccggtatc gggtgtgtcc gtggcgctca ttccaacctc   3600
```

-continued

```
cgtgtgtttg tgcaggtttc gcgtgttgca gtccctcgca ccggcacccg cagcgagggg   3660
ctcacgggtg ccggtgggtc gactagtcta ctcgacgacg cgtaccgcgc cggacgggca   3720
cagcgcgccg gcttcgagtg ccgccgcacg gccggcctcg ccgggttccg cggccagcac   3780
cgtcaccaca ccgtcgtcgt cctggtcgaa gacctccggc gccgtcaagg cgcacaggcc   3840
cgctcccacg cagacctccc ggtcggccgt cacacgcatg gctgctcctt tcgccgcggt   3900
caccaggtga ccgggagttc gttcacgccc tggatcgtcg tgcccgggcg cagggtcagc   3960
cggtccaccg gcaccgccag ccgcagaccg ggcagccgct cgaacagcgc cgtgaggatg   4020
acctccagtt cgaggcgggc caggttctgg ccgaggcact gatgcacccc gtagccgaac   4080
gccaggtggt ggcgggcctc gcgccgcacg tcgaaggcgt ccgggtcggc gaagacggag   4140
ccgtcgcggt tggcgatcga gttggtgacg atgacccccct cccccgcccg gatgcgctgc   4200
ccgtcgatct cgatgtccgc cgtcgcgatc cgcccgccgg cgatgtcggc gatggccaga   4260
tagcgcagca gctcctccac cgcgccgggc accagcgacg gatcggcgcg caacgcggcg   4320
tgctggtcgg gatgttcgag gagggtgatg acgctgagcg acgtcatcga cgccgtcgtc   4380
tcgtgtccgg cgaccagcag caggatcgcc gtcgacacca gctcctcccg gtcgatcgcg   4440
cccttctcca gctgctccct gacgagcgtg ctcagcaggc ccggccggga ctcgcctcgc   4500
aggctgtcca ccagagcgcc cagatagctc tccaggtcgt cccgggcggc acgcgcaccc   4560
gccgcgtccg gggactggat cagccgtgcg ctggcgtcct ggaagaagtc gtggtccgcg   4620
tagggcacac cgagcagacg gcagatcacc agggacggga cgggcagcgc gaactggctg   4680
accaggtcgg cgggcgggcc gcctgcgatc atctcgtcca ggaagccgtg cacgatctgc   4740
tcgacgtcgg cccgcatgcc cttgatgcgc cggacggtga actcgctgat ggtcatgcgc   4800
cgtttcggcc cgtgctcggg cgggtccagg ctgatgaacg ccggccggcg gtcccggaag   4860
ctctccaccc gcccggaggt ggcggggaag tcggcgtgtg tccggtcgga cgagagccgg   4920
gggtcggcca gcagcttgcg tgccgtgtcg tacccggtca ccagccatgc ctgccggccg   4980
tcgtagaggg tgacccgctg cagcgaaccc tcccggtccc ggaggtcgtt gtaccggtcg   5040
gggaggtggt aggggcaggt gcggtcactg gggaaggcgg gggcgcctga tgtgggcgtc   5100
gtaacggtct cggtcatcat atgcgatggt ccttcccgtg gggatgtcc gtgggggatg   5160
tccgtggaga tatcactgca ttgcgcgtga tgccggacac taggaaggtg ggggttgcac   5220
aggggttgca cgcagatgcg gaacctgaac ctccggagag tgccgatccc gcggattcga   5280
ttcaggtaag gctgagctaa ccatagggtg agtgtcgtga cgcgtgaacg aggcgggctg   5340
gagcgggcgc gtggcgccgc gctgaccggt tcggccgcac cggaggtgcg cccggagatc   5400
cgggcgtcct gggagcgttc gctggccgcc gccgtcgatc cggagcggtc ccggccctcg   5460
cacacctacc agccgggcga ggtcgccgag ctgcgcgccg gacatccgct ggcgcaggtc   5520
ctgccgctgc tgcgggagac cctcgtcgcc gcggccgagc aggccaggca cggtaccctc   5580
ccgccgcccc gcacggcacg ccgtcatgac ggtcaaccgt cggcgtcgtc ctatcgacga   5640
cagcaccgga tgccggacgg ggaacaggag caccgcccgt ctcgaccgct gcccttcctc   5700
gatacaaggc cgcacgagtg cggggcaggt tcagtcaagg gtcggcgcag ccgatcgcgt   5760
agcgacgccg caggcgccct tggcgggttc tgacctgcat tcgacactta gccgccatcg   5820
aggtagggcc caccgcagca cgcgctacag caccggcacc gagaacaccc tcagctctcg   5880
cgccgcaggc gcgcgcccgg tccggacggg cccggcccgc gggccggagg caggagcggg   5940
ccggagcccg gcccggccgg gcgccggcca cagcggcccg atcgctggcg gtgctcgatg   6000
```

```
accgccgcgc tgacgcgcgt cgacgcgggc gtgcccgcgc ttggtactga cgcgaaaagt   6060
gcggccaccg caggtcaggt ccccgtgggg gactgggcag ggagcttctg ggagcggcag   6120
gaccgcgcct tgcgggagaa gtaccgggcc cgccgtgagc tggccaggat cacgacgctg   6180
cgtcgcgttg cacgctgcgg acgctcctcg atgaacgacg gcggagacgt cgtcctgcgc   6240
tactcgcccg gcaccgggga ggacggctcg gcgtcggcgg gtttcggcgg actggtgacc   6300
tgcggcagcc tgtgggcctg cccggtctgc tcggccaaga tcagcgcccg ccgggcccgg   6360
gagctggaac acctgatcac ctggaacgcc gcccgcggcg gcaccgtcgc gctgctcagc   6420
ctgaccatgc gccaccacag cggccaccgc ctgcgcgacc tgcgccgagg gctgagcgcc   6480
gcgtggcgcc acgtcaccag ctcccgcggg tggaagcgct ggaagagcgt cttgggaatg   6540
gactacgtcc gcgggattga ggccacccac ggagcgaacg gctggcatct gcacatccac   6600
gccctgctga tcttccccgg cgacgtcacg gaggagatgc acgccctcac cgccgagatc   6660
tggacccgct ggtcgaccgg cctgcggcgc aagggcttcg acgccacgat cgcccacggc   6720
gtcgacgtcc gggtcggcac cggcgccctc gaacagctcg gccgctacat ctccaaactg   6780
gccttcgaga cctccggcgg ccggtggaag ctgggcaaga acggcagccg taccccgttc   6840
cagatcctcg ccgacgccct ggaccgagcc cgcgaccgag acctcgcgct ctgggcggag   6900
tgggagcagg ccagccacgg catgcagcag ctcgtgtggt ccaacggact caaggcggcc   6960
tgccagctcg acgagatcga cgacgagacg atcgcggagg aggacgacgg tggtgagttc   7020
gtcgcccagc tcccccgccg cacctgggag aaggtctacc ccgtcgccga agacctgatc   7080
atcgccaccc gcactggtgg ccccgaagca ggccgcgcct ggcttgacgc ccgcggcctg   7140
gcctatgacc acgagcgcga cacgagcgaa cgagcagtcc tgctcgacga gccggacccg   7200
ccgttcgcgt ggctgagggc cgctctcgcg gccgaagacc ccgagcagcg ccgggagcga   7260
cgccgccgct actaccgcac cgcacagacc aactgagctc gatgaggagc agaaccacga   7320
tggccgacac ctggacgatc agcccgctga tccgccccct gctgcgcaag ctcgatgagc   7380
gcggaggctg cgcctacccg caggacttcc cgcactgcca cggcgccgag atccagcaca   7440
ccgacggcac cgccgaatgc ttcaaccccg gccagccctg cccctaccca cgacccggcg   7500
cgcacgcctt cgtccacacc tgcgctgacg tcacccaccg gctcacccac cgctgcaccc   7560
gctgccgctg attcaccaca ggccatgcac ctatgcattg cccaatgatg atcttcggct   7620
gctgacgtcg tcgatacgac gacattactc aattctgttg tcccataaag catctggcct   7680
ctaat                                                               7685
```

<210> SEQ ID NO 47
<211> LENGTH: 390
<212> TYPE: PRT
<213> ORGANISM: Pseudonocardia autotrophica

<400> SEQUENCE: 47

```
Met Met Ile Val Thr Asp Glu Arg Gly His Ile Leu Trp Arg Glu Gly
1               5                   10                  15

Ala Arg Glu Val Leu Arg Arg Ala Glu Arg Val Glu Leu Val Glu Gly
            20                  25                  30

Thr Arg Trp Ser Glu Asp Ser Val Gly Thr Asn Ala Met Gly Thr Ala
        35                  40                  45

Leu Ser Asp Asp Arg Pro Val Arg Ile His Ser Ala Glu His Leu Val
    50                  55                  60
```

```
Ser Ala Tyr His Pro Trp Thr Cys Ala Ala Ala Pro Val His Asp Pro
65                  70                  75                  80

Glu Thr Gly Arg Gln Ile Gly Ala Val Asp Val Thr Gly Pro Glu Glu
                85                  90                  95

Ser Phe His Pro Met Thr Leu Ser Leu Val Thr Ala Ala Ala Arg Leu
            100                 105                 110

Ala Glu His Arg Leu Ala Ala Leu Leu Glu Asp Arg Asp Arg Arg Leu
        115                 120                 125

Arg Asp Thr Asn Leu Pro His Leu Ser Arg Leu Gly Asp Val Pro Gly
    130                 135                 140

Ala Leu Leu Ser Pro His Gly Arg Val Leu Ala Ala Thr Pro Ala His
145                 150                 155                 160

Arg Phe Pro Val Arg Val Thr Leu Pro Glu Arg Gly Asp Arg Ile Leu
                165                 170                 175

Leu Asp Gly Gly Ala Glu Ala Val Leu Glu Pro Leu Gly Glu Gly Trp
            180                 185                 190

Leu Leu Arg Val Pro Thr Pro Ser Gly Pro Val Leu Pro Ala Leu Thr
        195                 200                 205

Leu Pro Phe Leu Gly Ala Arg Ala Pro Val Ala Arg Arg Asp Gly Arg
    210                 215                 220

Pro Leu Arg Leu Gly Leu Arg His Ala Glu Val Leu Thr Leu Leu Ala
225                 230                 235                 240

Leu His Pro Glu Gly Leu Thr Ala Asp Gln Leu Ala Gly Ala Leu Tyr
                245                 250                 255

Gly Asp Glu Gly Arg Pro Ile Thr Val Arg Ala Glu Met His Arg Leu
            260                 265                 270

Arg Arg Cys Val Gly Glu Asp Thr Val Arg Thr Gln Pro Tyr Arg Leu
        275                 280                 285

Ala Ala Arg Val Asp Ala Asp Phe Leu Arg Leu Arg Glu Ala Leu Arg
    290                 295                 300

His Gly Arg Val Arg Asp Ala Ala Ala Glu Ala Ala Arg Gly Pro Leu
305                 310                 315                 320

Leu Pro Thr Ser Glu Ser Pro Gly Val Arg Ala Glu Arg Glu His Leu
                325                 330                 335

Val Ala Ser Thr Arg Thr Ala Val Leu Arg Ser Gly Asp Pro Glu Ala
            340                 345                 350

Leu Leu Ala Leu Leu Arg Ala Asp Pro Asp Ser Asp Pro Asp Thr Glu
        355                 360                 365

Leu Arg Asp Arg Leu Arg Arg Ala Leu Pro Asp Gly Asp His Arg Asp
    370                 375                 380

Leu Ala Leu Pro Asp Gly
385                 390
```

```
<210> SEQ ID NO 48
<211> LENGTH: 507
<212> TYPE: PRT
<213> ORGANISM: Pseudonocardia autotrophica

<400> SEQUENCE: 48

Met Ala Thr Tyr Ala Ala Pro Gly Gln Pro Asp Ser Val Val Ser Phe
1               5                   10                  15

Lys Pro Arg Tyr Asp His Phe Ile Gly Gly Glu Tyr Ile Ala Pro Ala
            20                  25                  30

Lys Gly Gln Tyr Phe Glu Asn Pro Thr Pro Ile Thr Gly Glu Asn Phe
        35                  40                  45
```

-continued

```
Thr Glu Val Ala Arg Gly Thr Ala Asp Asp Val Glu Lys Ala Leu Asp
    50                  55                  60

Ala Ala His Gly Ala Ala Pro Ala Trp Gly Lys Thr Ser Pro Thr Glu
65                  70                  75                  80

Arg Ala Asn Ile Leu Asn Lys Met Ala Asp Arg Ile Glu Ala Asn Leu
                85                  90                  95

Glu Ala Val Ala Ile Ala Glu Ser Trp Glu Asn Gly Lys Ala Cys Arg
            100                 105                 110

Glu Thr Leu Ala Ala Asp Ile Pro Leu Ala Ile Asp His Leu Arg Tyr
        115                 120                 125

Phe Ala Gly Ala Ile Arg Ala Gln Glu Gly Gly Leu Ser Gln Ile Asp
    130                 135                 140

Asp Asp Thr Val Ala Tyr His Phe His Glu Pro Leu Gly Val Val Gly
145                 150                 155                 160

Gln Ile Ile Pro Trp Asn Phe Pro Ile Leu Met Ala Ile Trp Lys Leu
                165                 170                 175

Ala Pro Ala Leu Ala Ala Gly Asn Ala Ile Val Leu Lys Pro Ala Glu
            180                 185                 190

Gln Thr Pro Val Ser Ile His Val Leu Leu Asp Leu Val Ala Asp Leu
        195                 200                 205

Leu Pro Pro Gly Val Leu Asn Ile Val Asn Gly Phe Gly Val Glu Ala
    210                 215                 220

Gly Lys Pro Leu Ala Ser Asn Lys Arg Ile Ser Lys Ile Ala Phe Thr
225                 230                 235                 240

Gly Glu Thr Thr Thr Gly Arg Leu Ile Met Gln Tyr Ala Ser Glu Asn
                245                 250                 255

Leu Ile Pro Val Thr Leu Glu Leu Gly Gly Lys Ser Pro Asn Ile Phe
            260                 265                 270

Phe Asp Asp Val Ala Ser Gln Gln Asp Ala Phe Tyr Asp Lys Ala Leu
        275                 280                 285

Glu Gly Phe Ala Met Phe Ala Leu Asn Gln Gly Glu Val Cys Thr Cys
    290                 295                 300

Pro Ser Arg Ala Leu Ile Gln Gly Gly Ile Tyr Gln Glu Phe Leu Glu
305                 310                 315                 320

Gln Ala Val Lys Arg Thr Glu Gln Ile Lys Gln Gly Asn Pro Leu Asp
                325                 330                 335

Thr Asp Thr Gln Ile Gly Ala Gln Ala Ser Asn Asp Gln Phe Glu Lys
            340                 345                 350

Ile Leu Ser Tyr Ile Asp Ile Gly Arg Gln Glu Gly Ala Lys Val Leu
        355                 360                 365

Thr Gly Gly Glu Lys Ala Asp Leu Gly Gly Asp Leu Ser Gly Gly Tyr
    370                 375                 380

Tyr Ile Lys Pro Thr Val Phe Glu Gly Asn Asn Gln Met Arg Ile Phe
385                 390                 395                 400

Gln Glu Glu Ile Phe Gly Pro Val Val Ser Val Ala Arg Phe Ser Asp
                405                 410                 415

Tyr Asp Asp Ala Ile Arg Thr Ala Asn Asp Thr Leu Tyr Gly Leu Gly
            420                 425                 430

Ala Gly Val Trp Ser Arg Asp Thr Asn Thr Ala Tyr Arg Ala Gly Arg
        435                 440                 445

Asp Ile Gln Ala Gly Arg Val Trp Val Asn Asn Tyr His Ala Tyr Pro
    450                 455                 460
```

```
Ala His Ala Ala Phe Gly Gly Tyr Lys Gln Ser Gly Ile Gly Arg Glu
465                 470                 475                 480

Asn His Lys Gln Met Leu Asp His Tyr Gln Gln Thr Lys Asn Val Leu
                485                 490                 495

Gln Ser Tyr Ser Pro Asn Ala Leu Gly Phe Phe
            500                 505


<210> SEQ ID NO 49
<211> LENGTH: 2100
<212> TYPE: DNA
<213> ORGANISM: Pseudonocardia autotrophica

<400> SEQUENCE: 49

ctcccgccgc cccgcacggc acgccgtcat gacggtcaac cgtcggcgtc gtcctatcga     60

cgacagcacc ggatgccgga cggggaacag gagcaccgcc cgtctcgacc gctgcccttc    120

ctcgatacaa ggccgcacga gtgcggggca ggttcagtca agggtcggcg cagccgatcg    180

cgtagcgacg ccgcaggcgc ccttggcggg ttctgacctg cattcgacac ttagccgcca    240

tcgaggtagg gcccaccgca gcacgcgcta cagcaccggc accgagaaca ccctcagctc    300

tcgcgccgca ggcgcgcgcc cggtccggac gggcccggcc cgcgggccgg aggcaggagc    360

gggccggagc ccggcccggc cgggcgccgg ccacagcggc ccgatcgctg gcggtgctcg    420

atgaccgccg cgctgacgcg cgtcgacgcg ggcgtgcccg cgcttggtac tgacgcgaaa    480

agtgcggcca ccgcaggtca ggtccccgtg gggactgggc cagggagctt ctgggagcgg    540

caggaccgcg ccttgcggga gaagtaccgg gcccgccgtg agctggccag gatcacgacg    600

ctgcgtcgcg ttgcacgctg cggacgctcc tcgatgaacg acggcggaga cgtcgtcctg    660

cgctactcgc ccggcaccgg ggaggacggc tcggcgtcgg cgggtttcgg cggactggtg    720

acctgcggca gcctgtgggc ctgcccggtc tgctcggcca agatcagcgc ccgccgggcc    780

cgggagctgg aacacctgat cacctggaac gccgcccgcg gcggcaccgt cgcgctgctc    840

agcctgacca tgcgccacca cagcggccac cgcctgcgcg acctgcgccg agggctgagc    900

gccgcgtggc gccacgtcac cagctcccgc gggtggaagc gctggaagag cgtcttggga    960

atggactacg tccgcgggat tgaggccacc cacggagcga acggctggca tctgcacatc   1020

cacgccctgc tgatcttccc cggcgacgtc acggaggaga tgcacgccct caccgccgag   1080

atctggaccc gctggtcgac cggcctgcgg cgcaagggct tcgacgccac gatcgcccac   1140

ggcgtcgacg tccgggtcgg caccggcgcc ctcgaacagc tcggccgcta catctccaaa   1200

ctggccttcg agacctccgg cggccggtgg aagctgggca agaacggcag ccgtaccccg   1260

ttccagatcc tcgccgacgc cctggaccga gcccgcgacc gagacctcgc gctctgggcg   1320

gagtgggagc aggccagcca cggcatgcag cagctcgtgt ggtccaacgg actcaaggcg   1380

gcctgccagc tcgacgagat cgacgacgag acgatcgcgg aggaggacga cggtggtgag   1440

ttcgtcgccc agctcccccg ccgcacctgg gagaaggtct accccgtcgc cgaagacctg   1500

atcatcgcca cccgcactgg tggccccgaa gcaggccgcg cctggcttga cgcccgcggc   1560

ctggcctatg accacgagcg cgacacgagc gaacgagcag tcctgctcga cgagccggac   1620

ccgccgttcg cgtggctgag ggccgctctc gcggccgaag accccgagca gcgccgggag   1680

cgacgccgcc gctactaccg caccgcacag accaactgag ctcgatgagg agcagaacca   1740

cgatggccga cacctggacg atcagcccgc tgatccgccc cctgctgcgc aagctcgatg   1800

agcgcggagg ctgcgcctac ccgcaggact tcccgcactg ccacggcgcc gagatccagc   1860
```

```
acaccgacgg caccgccgaa tgcttcaacc ccggccagcc ctgcccctac ccacgacccg   1920

gcgcgcacgc cttcgtccac acctgcgctg acgtcaccca ccggctcacc caccgctgca   1980

cccgctgccg ctgattcacc acaggccatg cacctatgca ttgcccaatg atgatcttcg   2040

gctgctgacg tcgtcgatac gacgacatta ctcaattctg ttgtcccata aagcatctgg   2100


<210> SEQ ID NO 50
<211> LENGTH: 432
<212> TYPE: PRT
<213> ORGANISM: Pseudonocardia autotrophica

<400> SEQUENCE: 50

Met Thr Ala Ala Leu Thr Arg Val Asp Ala Gly Val Pro Ala Leu Gly
1               5                   10                  15

Thr Asp Ala Lys Ser Ala Ala Thr Ala Gly Gln Val Pro Val Gly Asp
            20                  25                  30

Trp Ala Gly Ser Phe Trp Glu Arg Gln Asp Arg Ala Leu Arg Glu Lys
        35                  40                  45

Tyr Arg Ala Arg Arg Glu Leu Ala Arg Ile Thr Thr Leu Arg Arg Val
    50                  55                  60

Ala Arg Cys Gly Arg Ser Ser Met Asn Asp Gly Gly Asp Val Val Leu
65                  70                  75                  80

Arg Tyr Ser Pro Gly Thr Gly Glu Asp Gly Ser Ala Ser Ala Gly Phe
                85                  90                  95

Gly Gly Leu Val Thr Cys Gly Ser Leu Trp Ala Cys Pro Val Cys Ser
            100                 105                 110

Ala Lys Ile Ser Ala Arg Arg Ala Arg Glu Leu Glu His Leu Ile Thr
        115                 120                 125

Trp Asn Ala Ala Arg Gly Gly Thr Val Ala Leu Leu Ser Leu Thr Met
    130                 135                 140

Arg His His Ser Gly His Arg Leu Arg Asp Leu Arg Arg Gly Leu Ser
145                 150                 155                 160

Ala Ala Trp Arg His Val Thr Ser Ser Arg Gly Trp Lys Arg Trp Lys
                165                 170                 175

Ser Val Leu Gly Met Asp Tyr Val Arg Gly Ile Glu Ala Thr His Gly
            180                 185                 190

Ala Asn Gly Trp His Leu His Ile His Ala Leu Leu Ile Phe Pro Gly
        195                 200                 205

Asp Val Thr Glu Glu Met His Ala Leu Thr Ala Glu Ile Trp Thr Arg
    210                 215                 220

Trp Ser Thr Gly Leu Arg Arg Lys Gly Phe Asp Ala Thr Ile Ala His
225                 230                 235                 240

Gly Val Asp Val Arg Val Gly Thr Gly Ala Leu Glu Gln Leu Gly Arg
                245                 250                 255

Tyr Ile Ser Lys Leu Ala Phe Glu Thr Ser Gly Gly Arg Trp Lys Leu
            260                 265                 270

Gly Lys Asn Gly Ser Arg Thr Pro Phe Gln Ile Leu Ala Asp Ala Leu
        275                 280                 285

Asp Arg Ala Arg Asp Arg Asp Leu Ala Leu Trp Ala Glu Trp Glu Gln
    290                 295                 300

Ala Ser His Gly Met Gln Gln Leu Val Trp Ser Asn Gly Leu Lys Ala
305                 310                 315                 320

Ala Cys Gln Leu Asp Glu Ile Asp Asp Glu Thr Ile Ala Glu Glu Asp
                325                 330                 335
```

-continued

```
Asp Gly Gly Glu Phe Val Ala Gln Leu Pro Arg Arg Thr Trp Glu Lys
            340                 345                 350

Val Tyr Pro Val Ala Glu Asp Leu Ile Ile Ala Thr Arg Thr Gly Gly
        355                 360                 365

Pro Glu Ala Gly Arg Ala Trp Leu Asp Ala Arg Gly Leu Ala Tyr Asp
    370                 375                 380

His Glu Arg Asp Thr Ser Glu Arg Ala Val Leu Leu Asp Glu Pro Asp
385                 390                 395                 400

Pro Pro Phe Ala Trp Leu Arg Ala Ala Leu Ala Ala Glu Asp Pro Glu
                405                 410                 415

Gln Arg Arg Glu Arg Arg Arg Arg Tyr Tyr Arg Thr Ala Gln Thr Asn
            420                 425                 430


<210> SEQ ID NO 51
<211> LENGTH: 33
<212> TYPE: DNA
<213> ORGANISM: Pseudonocardia autotrophica

<400> SEQUENCE: 51

ccgtcatgac ggtcaaccgt cggcgtcgtc cta                                   33
```